(12) United States Patent
Yurkow et al.

(10) Patent No.: US 7,615,533 B2
(45) Date of Patent: *Nov. 10, 2009

(54) TPO PEPTIDE COMPOUNDS FOR TREATMENT OF ANEMIA

(75) Inventors: Edward J. Yurkow, Hillsborough, NJ (US); Brian R. MacDonald, Newtown Square, PA (US); Jeffery K. Weis, Whitehouse Station, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 179 days.

This patent is subject to a terminal disclaimer.

(21) Appl. No.: 11/354,065

(22) Filed: Feb. 14, 2006

(65) Prior Publication Data

US 2008/0119384 A1    May 22, 2008

Related U.S. Application Data

(63) Continuation-in-part of application No. 11/181,049, filed on Jul. 14, 2005, now abandoned.

(60) Provisional application No. 60/601,921, filed on Aug. 16, 2004.

(51) Int. Cl.
*A61K 38/00* (2006.01)
*A61K 39/00* (2006.01)
*C07K 5/00* (2006.01)
*C07K 7/00* (2006.01)

(52) U.S. Cl. .................. 514/3; 514/2; 514/13; 514/14; 514/15; 514/17; 530/300; 530/324; 530/325; 530/326; 530/327

(58) Field of Classification Search ........................ None
See application file for complete search history.

(56) References Cited

U.S. PATENT DOCUMENTS

| | | | |
|---|---|---|---|
| 6,251,864 B1 * | 6/2001 | Dower et al. ................... | 514/13 |
| 2002/0165178 A1 | 11/2002 | Schetter et al. | |
| 2002/0187124 A1 | 12/2002 | Takahashi | |
| 2004/0028649 A1 | 2/2004 | Gianni | |
| 2005/0282277 A1 * | 12/2005 | MacDonald et al. ........ | 435/372 |
| 2006/0040866 A1 * | 2/2006 | MacDonald et al. .......... | 514/13 |
| 2008/0119384 A1 | 5/2008 | Yurkow et al. | |

FOREIGN PATENT DOCUMENTS

| WO | WO 95/21626 A | 8/1995 |
|---|---|---|
| WO | WO 2004/026332 A | 4/2004 |
| WO | WO 2005/023834 A | 3/2005 |

OTHER PUBLICATIONS

Merck manual, Etiology of Anemia, pp. 1-2. Accessed Jun. 10, 2008.*
Merck manual, Evaluation of Anemia, pp. 1-4. Accessed Jun. 10, 2008.*
Merck manual, Introduction to Anemia, p. 1. Accessed Jun. 10, 2008.*
Merck manual, Anemia of Chronic Disease, pp. 1-2. Accessed Jun. 10, 2008.*
Merck manual, Treatment of Anemia, p. 1. Accessed Jun. 10, 2008.*
Merck manual, Aplastic Anemia, pp. 1-3, Accessed Jun. 10, 2008.*
Merck manual, Hypoproliferative Anermia, pp. 1-2. Accessed Jun. 10, 2008.*
Merck manual, Iron Deficiency Anemia, pp. 1-5. Accessed Jun. 10, 2008.*
Merck manual, Megaloblastic Macrocytic Anemias, pp. 1-3. Accessed Jun. 10, 2008.*
Merck manual, Myelophthisic Anemia, pp. 1-2. Accessed Jun. 10, 2008.*
De Serres, M, Ellis B, Dillberger JE, Rudolph SK, Hutchins JT, Boytos CM, Weigl DL, DePrince RB, Immunogenicity of Throbopoietin Mimetic Peptide GW395058 in BALB/c Mice and New Zealand White Rabbits: Evaluation of the Potential for Throbopoietin Neutralizing Antibody Production in Man, Stem Cells, 1999, 17: 203-209.*
Zdenko P and Slaninova J, The 1- and 2-Naphthylalanine Analogs of Oxytocin and Vasopressin, Coolect. Czech. Chem. Commun., 1995, 60: 2170-2177.*
Case B.C. et al: "The pharmacokinetics and pharmacodynamics of GW39505, a peptide agonist of the thrombopoietin receptor, in the dog, a large-animal model of chemotherapy-induced thrombocytopenia" Stem Cells, Alphamed Press, Dayton, Oh, vol. 18, No. 5, 2000, pp. 360-365, XP002421199, ISSN: 1066-5099.
De Serres M. et al: "Pharmacokinetics and hematological effects of the PEGylated thrombopoietin peptide mimetic GW395058 in rats and monkeys after intravenous or subcutaneous administration" Stem Cells, Alphamed Press, Dayton, OH, US, vol. 17, No. 6, 1999, pp. 316-326, XP002421200 ISSN: 1066-5099.
Singer S.C. et al.: "Pegylated thrombopoietin (TPO)-Mimetic peptides bind human to TPO receptor causing proliferation and maturation of megakaryocytes in vitro" Blood, W.B. Saunders Company, Orlando, FL, US, vol. 92, No. 10 Suppl PT1-2, Nov. 15, 1998, p. 568A, XP009079489.
International Search Report dated Apr. 26, 2007 for corresponding Appln. No. PCT/US2006/005322.

* cited by examiner

*Primary Examiner*—Cecilia Tsang
*Assistant Examiner*—Julie Ha
(74) *Attorney, Agent, or Firm*—Laura Donnelly

(57) ABSTRACT

Peptide compounds that bind to and activate the thrombopoietin receptor (c-mpl or TPO-R) or otherwise act as a TPO agonist are disclosed.

13 Claims, 14 Drawing Sheets

Figure 1 Effect of Treatment on Hemoglobin Levels
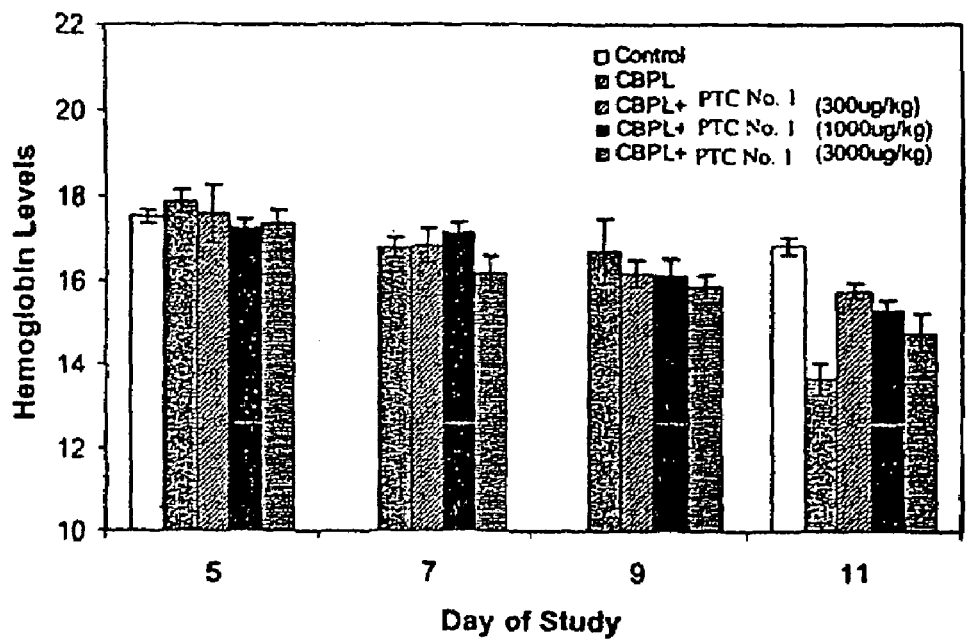
PEGylated TPO Compound No. 1 = PTC No. 1
Figure 2 Effect of Treatment on RBC Count
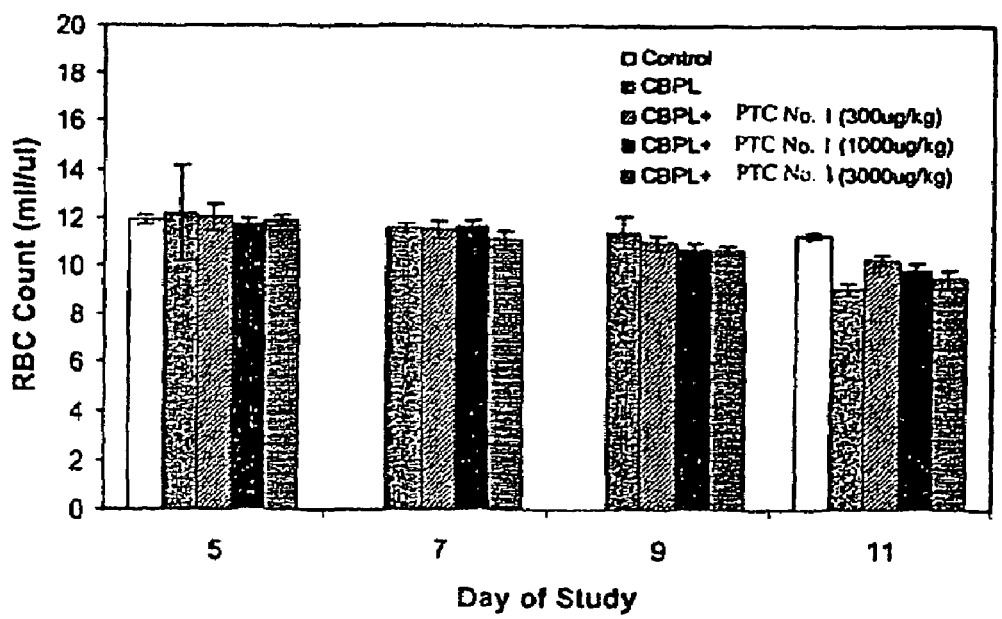
PEGylated TPO Compound No. 1 = PTC No. 1

Figure 3 Effect of Treatment on Hematocrit
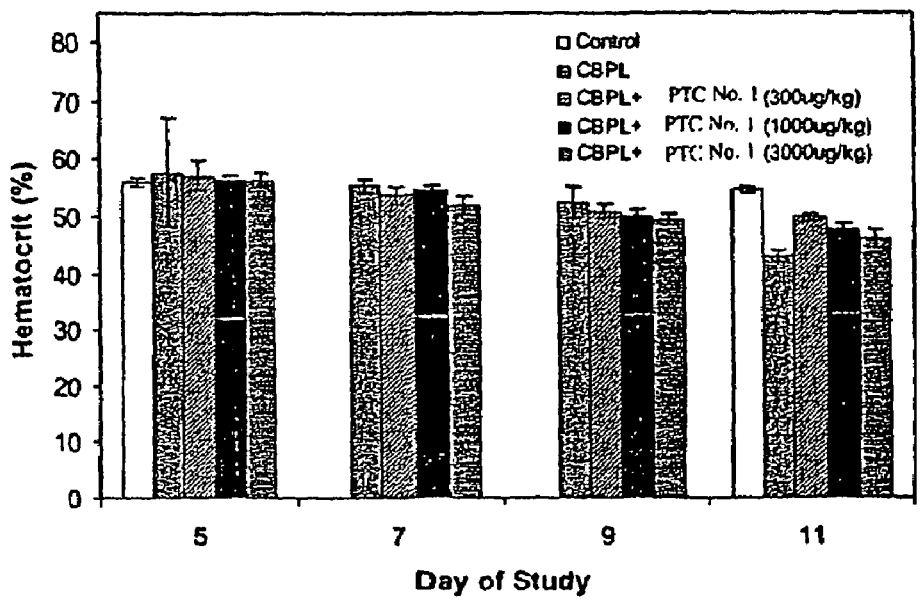
PEGylated TPO Compound No. 1 = PTC No. 1
Figure 4 Effect of Treatment on Body Weight of a Subset of Mice
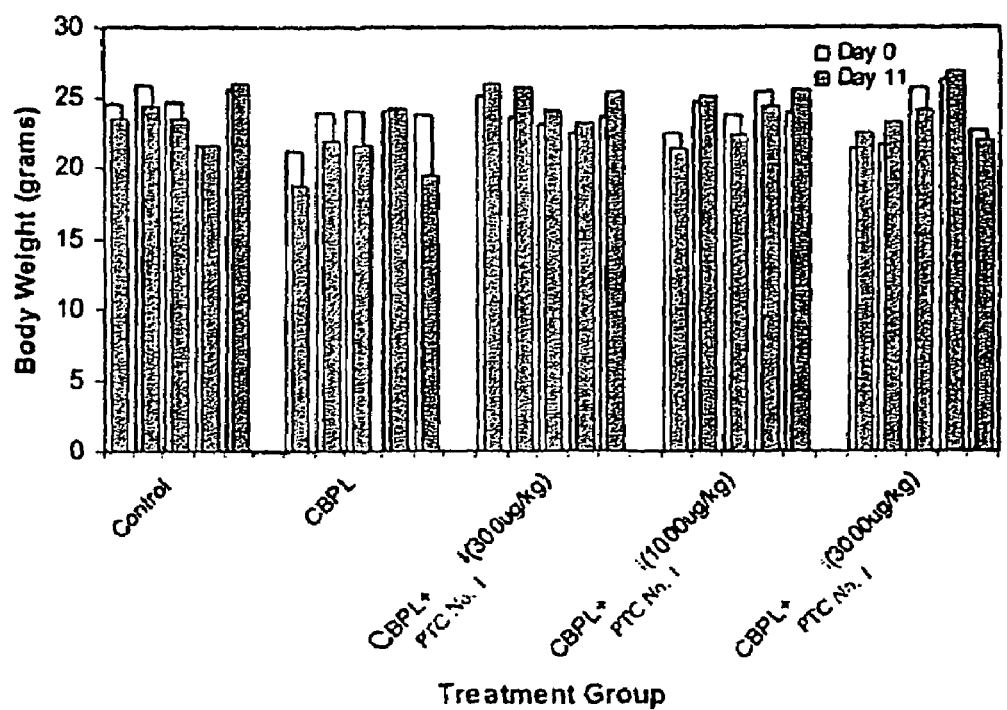
PEGylated TPO Compound No. 1 = PTC No. 1

Figure 5 Effect of Treatment on Hemoglobin Levels
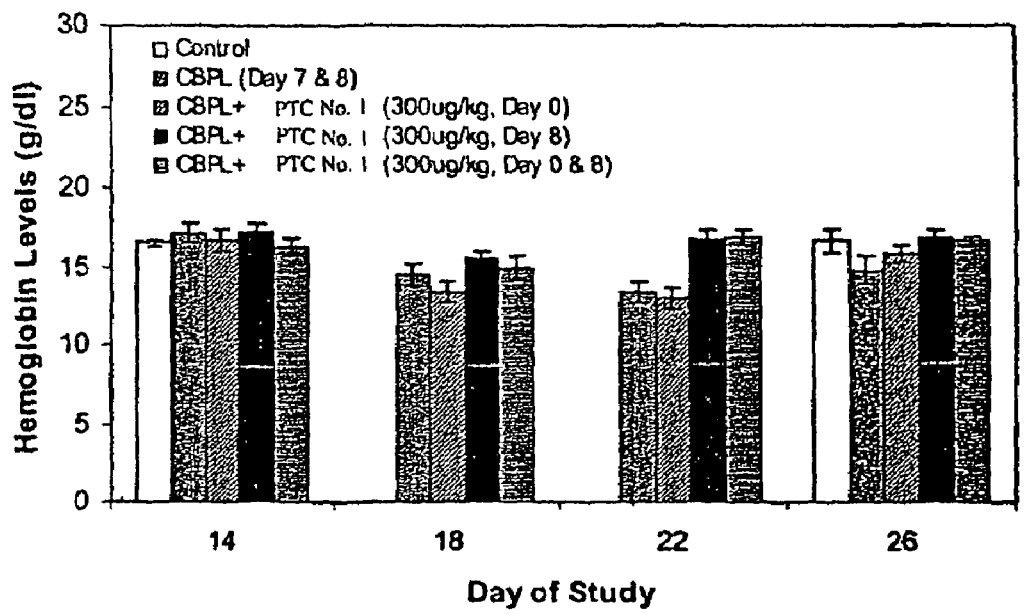
PEGylated TPO Compound No. 1 = PTC No. 1
Figure 6 Effect of Treatment on RBC Count
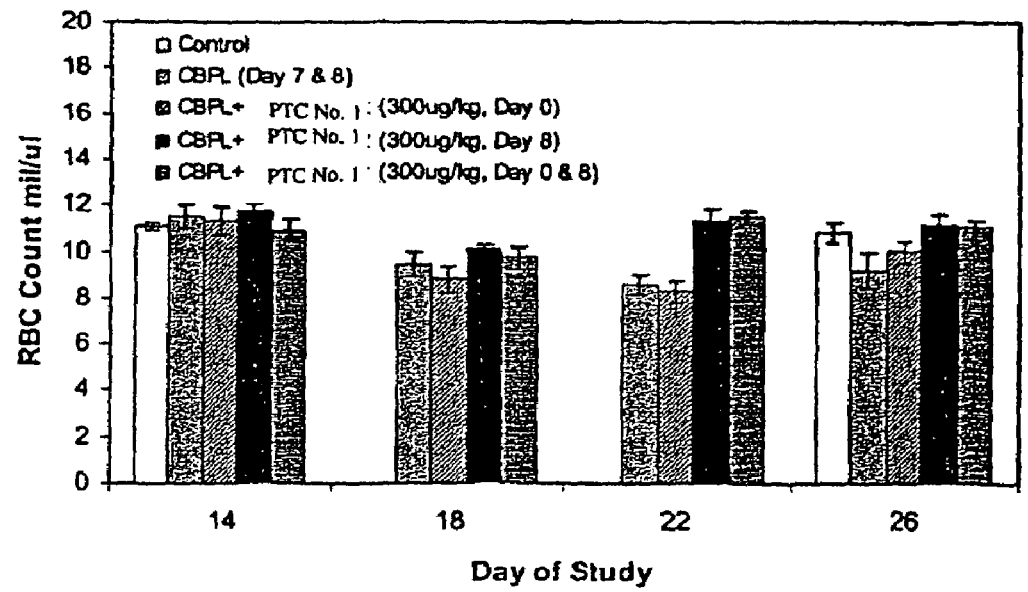
PEGylated TPO Compound No. 1 = PTC No. 1

Figure 7 Effect of Treatment on Hematocrit
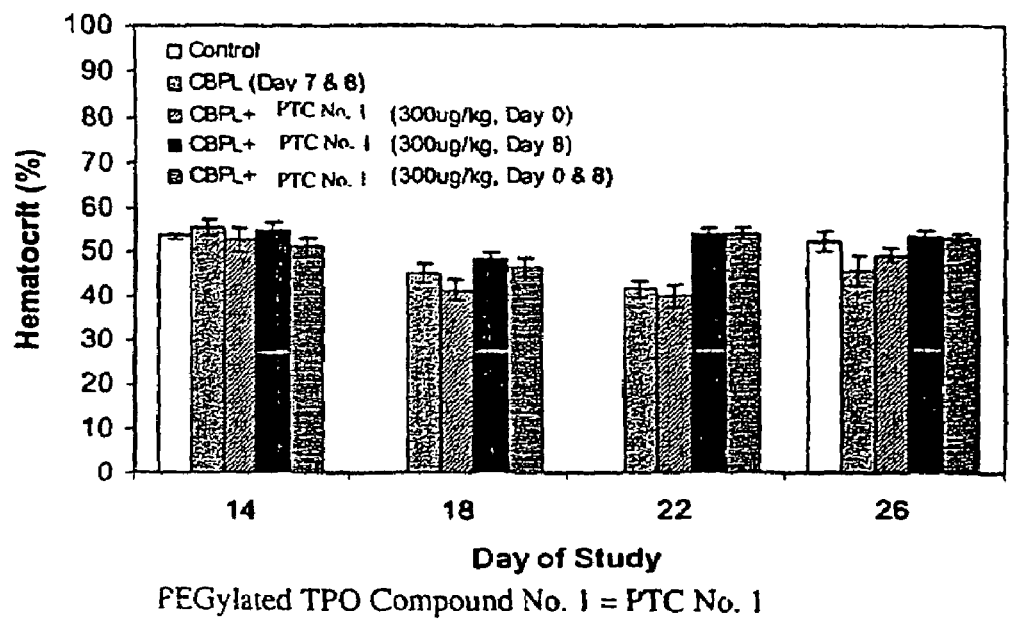
PEGylated TPO Compound No. 1 = PTC No. 1
Figure 8 Effect of Treatment on Body Weight of a Subset of Mice
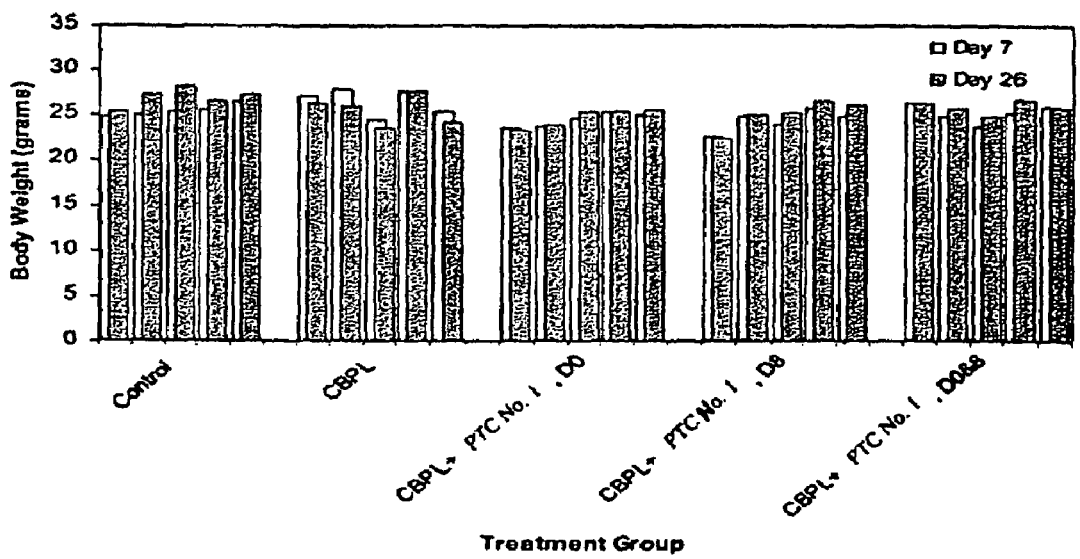
PEGylated TPO Compound No. 1 = PTC No. 1

Figure 9: Effect of Treatment on Hemoglobin Levels
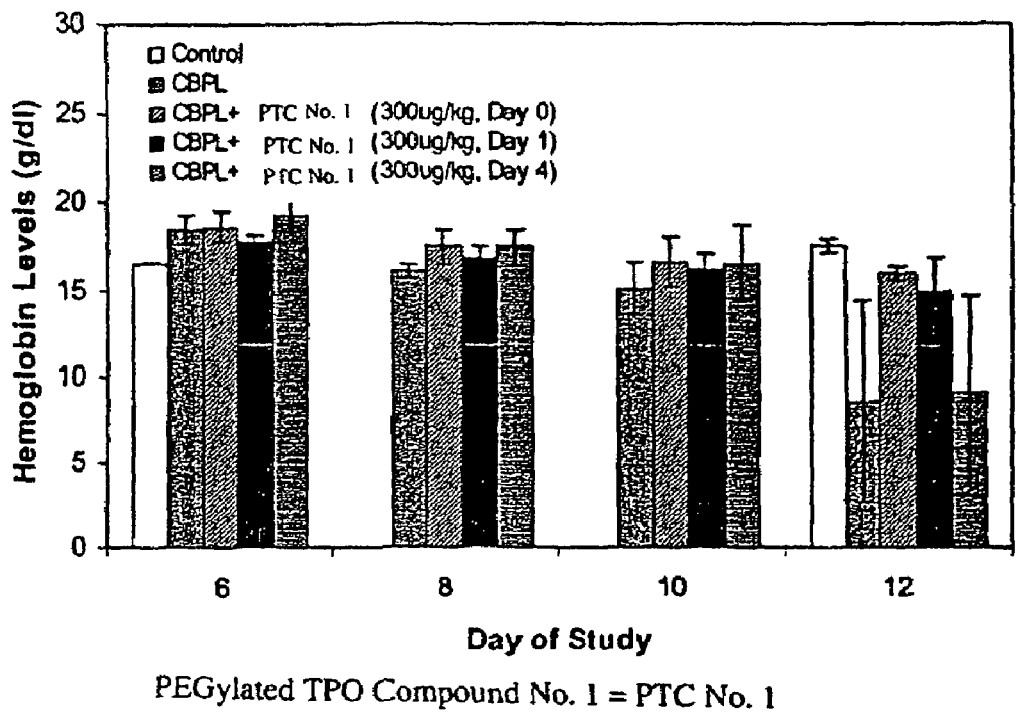
PEGylated TPO Compound No. 1 = PTC No. 1
Figure 10: Effect of Treatment on RBC Count
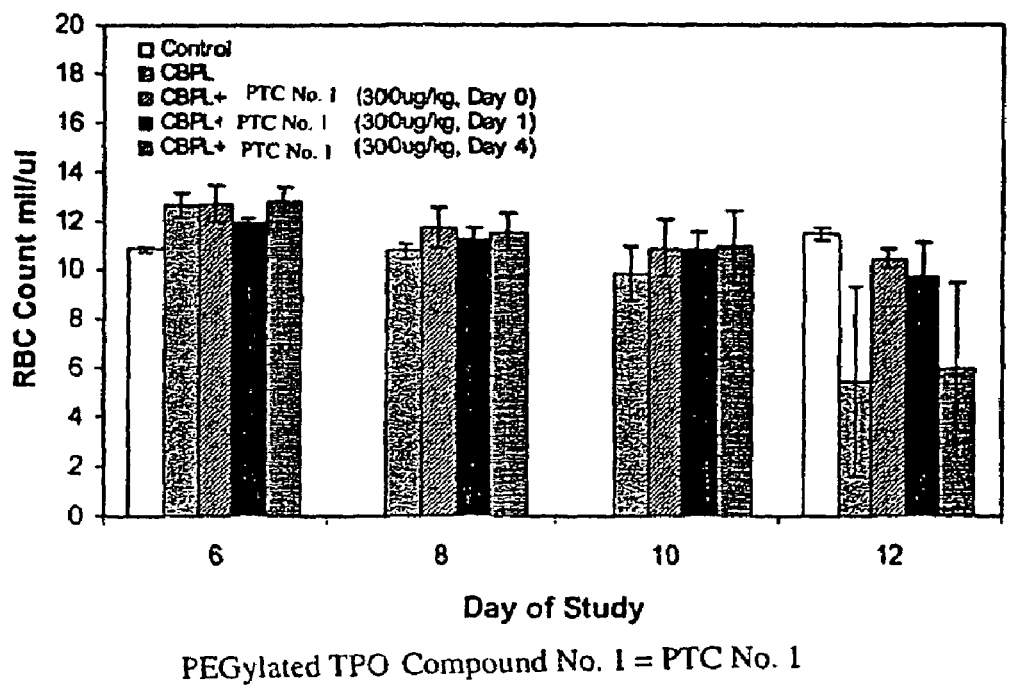
PEGylated TPO Compound No. 1 = PTC No. 1

Figure 11: Effect of Treatment on Hematocrit
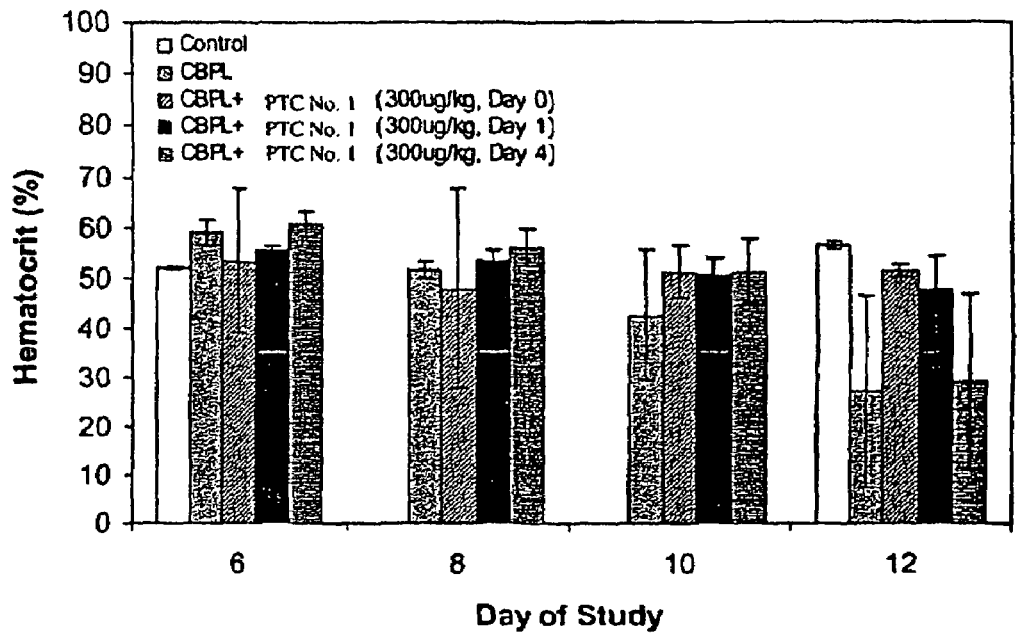
Figure 12: Effect of Treatment on Body Weight of a Subset of Mice
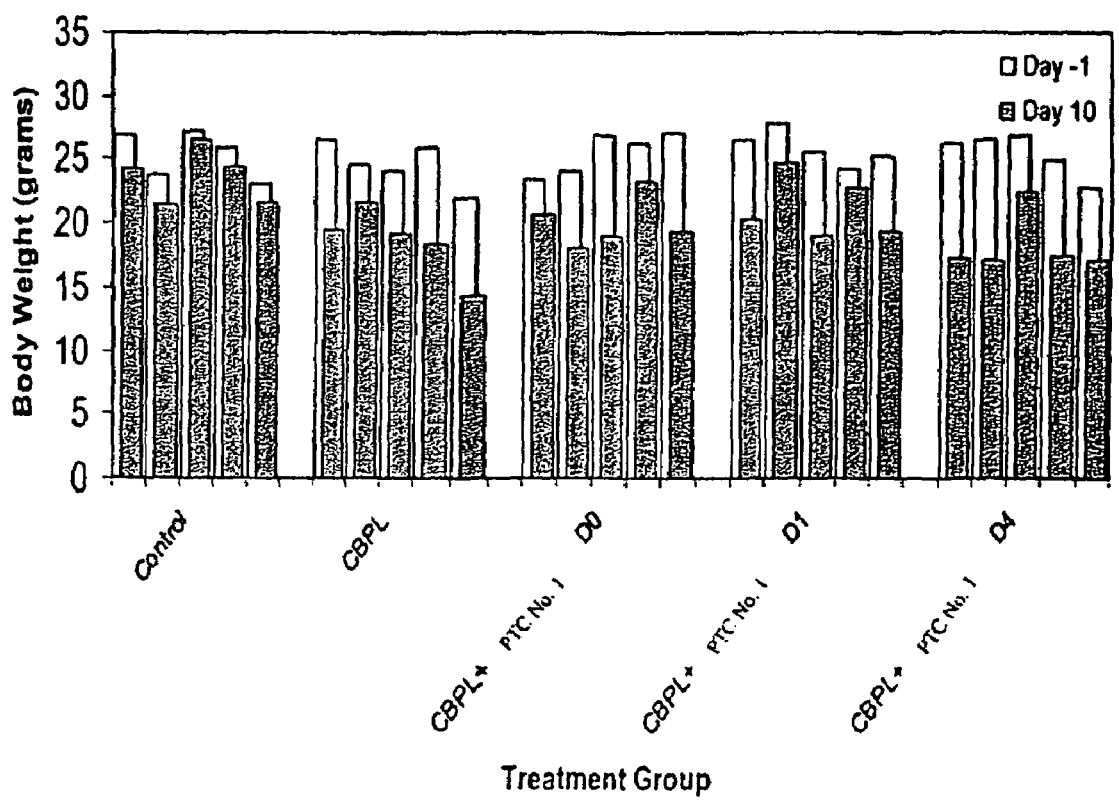

Figure 13: Effect of Treatment on Hematocrit
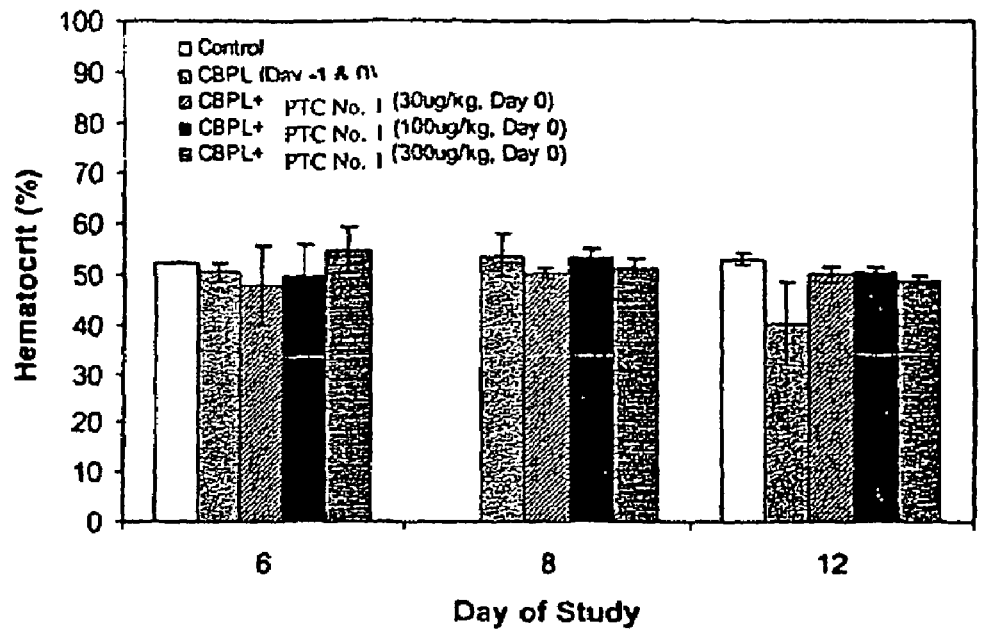
PEGylated TPO Compound No. 1 = PTC No. 1
Figure 14: Effect of Treatment on Body Weight for a Subset of Mice
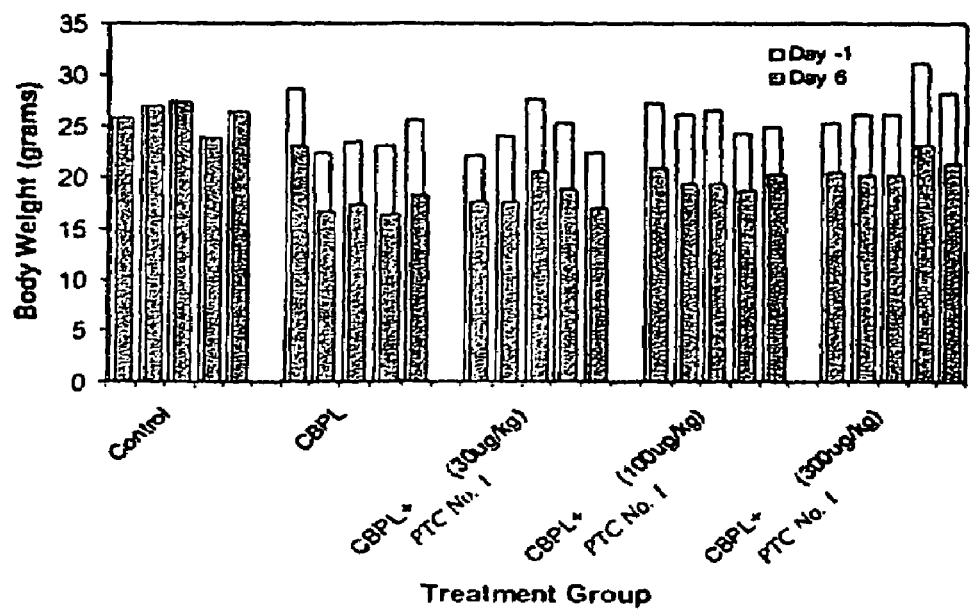
PEGylated TPO Compound No. 1 = PTC No. 1

PEGylated TPO Compound No. 1 = PTC No. 1

PTC No. 1 : Prevention of CIA, CIT in Mice – Mechanistic study

- Performed IHC on heart, brain and kidneys for fibrinogen

PEGylated TPO Compound No. 1 = PTC No. 1

PEGylated TPO Compound No. 1 = PTC No. 1

Fig. 20: Effect of PEGylated TPO Compound No. 1 (PTC No. 1) on TPO Receptor Activation in Baf/3 Cells PEGylated TPO Compound No. 1 = PTC No. 1

```
                         SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Variable amino acid

<400> SEQUENCE: 1

Trp Ser Xaa Trp Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Cys, Leu, Met, Pro, Gln or Val
<220> FEATURE:
<221> NAME/KEY: MOD_RES
<222> LOCATION: (2)
<223> OTHER INFORMATION: Phe, Lys, Leu, Asn, Gln, Arg, Ser, Thr
      or Val
<220> FEATURE:
<221> NAME/KEY: MOD_RES
<222> LOCATION: (3)
<223> OTHER INFORMATION: Cys, Phe, Ile, Leu, Met, Arg, Ser, Val
      or Trp
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (5)
<223> OTHER INFORMATION: Ala, Asp, Glu, Gly, Lys, Met, Gln, Arg,
      Ser, Thr, Val or Tyr
<220> FEATURE:
<221> NAME/KEY: MOD_RES
<222> LOCATION: (6)
<223> OTHER INFORMATION: 2-Nal
<220> FEATURE:
```

```
<221> NAME/KEY: MOD_RES
<222> LOCATION: (7)
<223> OTHER INFORMATION: Cys, Gly, Ile, Lys, Leu, Met, Asn, Arg
      or Val

<400> SEQUENCE: 2

Xaa Xaa Xaa Xaa Xaa Xaa Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (3)
<223> OTHER INFORMATION: Cys, Leu, Met, Pro, Gln or Val
<220> FEATURE:
<221> NAME/KEY: MOD_RES
<222> LOCATION: (4)
<223> OTHER INFORMATION: Phe, Lys, Leu, Asn, Gln, Arg, Ser, Thr
      or Val
<220> FEATURE:
<221> NAME/KEY: MOD_RES
<222> LOCATION: (5)
<223> OTHER INFORMATION: Cys, Phe, Ile, Leu, Met, Arg, Ser, Val
      or Trp
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (7)
<223> OTHER INFORMATION: Ala, Asp, Glu, Gly, Lys, Met, Gln, Arg, Ser,
      Thr, Val or Tyr
<220> FEATURE:
<221> NAME/KEY: MOD_RES
<222> LOCATION: (8)
<223> OTHER INFORMATION: 2-Nal
<220> FEATURE:
<221> NAME/KEY: MOD_RES
<222> LOCATION: (9)
<223> OTHER INFORMATION: Cys, Gly, Ile, Lys, Leu, Met, Asn, Arg or Val

<400> SEQUENCE: 3

Xaa Gly Xaa Xaa Xaa Xaa Xaa Xaa Xaa
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ala, Cys, Glu, Gly, Ile, Leu, Met, Pro,
      Arg, Gln, Ser, Thr or Val
<220> FEATURE:
<221> NAME/KEY: MOD_RES
<222> LOCATION: (2)
<223> OTHER INFORMATION: Ala, Cys, Asp, Glu, Lys, Leu, Gln, Arg,
      Ser, Thr or Val
<220> FEATURE:
<221> NAME/KEY: MOD_RES
```

```
<222> LOCATION: (4)
<223> OTHER INFORMATION: Cys, Leu, Met, Pro, Gln or Val
<220> FEATURE:
<221> NAME/KEY: MOD_RES
<222> LOCATION: (5)
<223> OTHER INFORMATION: Phe, Lys, Leu, Asn, Gln, Arg, Ser, Thr
      or Val
<220> FEATURE:
<221> NAME/KEY: MOD_RES
<222> LOCATION: (6)
<223> OTHER INFORMATION: Cys, Phe, Ile, Leu, Met, Arg, Ser, Val
      or Trp
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (8)
<223> OTHER INFORMATION: Ala, Asp, Glu, Gly, Lys, Met, Gln, Arg,
      Ser, Thr, Val or Tyr
<220> FEATURE:
<221> NAME/KEY: MOD_RES
<222> LOCATION: (9)
<223> OTHER INFORMATION: 2-Nal
<220> FEATURE:
<221> NAME/KEY: MOD_RES
<222> LOCATION: (10)
<223> OTHER INFORMATION: Cys, Gly, Ile, Lys, Leu, Met, Asn, Arg or Val
<220> FEATURE:
<223> OTHER INFORMATION: see specification as filed for detailed
      description of substitutions and preferred embodiments

<400> SEQUENCE: 4

Xaa Xaa Gly Xaa Xaa Xaa Xaa Xaa Xaa Xaa
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal
<220> FEATURE:
<221> NAME/KEY: MOD_RES
<222> LOCATION: (14)
<223> OTHER INFORMATION: Sar

<400> SEQUENCE: 5

Ile Glu Gly Pro Thr Leu Arg Gln Xaa Leu Ala Ala Arg Xaa
1               5                   10

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal
<220> FEATURE:
<221> NAME/KEY: MOD_RES
<222> LOCATION: (14)
<223> OTHER INFORMATION: Sar
<220> FEATURE:
<221> NAME/KEY: MOD_RES
<222> LOCATION: (16)
```

```
-continued
<223> OTHER INFORMATION: Sar
<220> FEATURE:
<221> NAME/KEY: MOD_RES
<222> LOCATION: (21)
<223> OTHER INFORMATION: 2-Nal

<400> SEQUENCE: 6

Ile Glu Gly Pro Thr Leu Arg Gln Xaa Leu Ala Ala Arg Xaa Lys Xaa
1               5                   10                  15

Arg Ala Ala Leu Xaa Gln Arg Leu Thr Pro Gly Glu Ile
            20                  25
```

TPO PEPTIDE COMPOUNDS FOR TREATMENT OF ANEMIA

CROSS REFERENCE TO RELATED APPLICATIONS

This application, which is a continuation-in-part, claims priority to U.S. application Ser. No. 11/181,049, filed on Jul. 14, 2005 now abandoned, and U.S. Application Ser. No. 60/601,921, filed Aug. 16, 2004, the entire contents of which are incorporated herein by reference.

FIELD OF THE INVENTION

The present invention provides peptide compounds that bind to and activate the thrombopoietin receptor (c-mpl or TPO-R) or otherwise act as a thrombopoietin ("TPO") agonist. The invention has application in the fields of biochemistry and medicinal chemistry and particularly provides TPO agonists for use in the treatment of human disease. The peptide compounds of the invention may be used to treat anemia and/or prevent the development of anemia and/or maintain normal production of red blood cells.

BACKGROUND OF THE INVENTION

The gene encoding TPO has been cloned and characterized. See Kuter et al. Proc. Natl. Acad. Sci. USA 91:11104-11108 (1994); Barley et al. Cell 77:1117-1124 (1994); Kaushansky et al. Nature 369:568-571 (1994); Wendling et al. Nature 369:571-574 (1994); and Sauvage et al. Nature 369: 533-538 (1994). TPO is a glycoprotein with at least two forms, with apparent molecular masses of 25 kDa and 31 kDa, with a common N-terminal amino acid sequence. See, Bartley et al. Cell 77:1117-1124 (1994). TPO appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO-R (also known as c-mpl) have been described. See Vigon et al. Proc. Natl. Acad. Sci. USA 89:5640-5644 (1992). TPO-R is a member of the hematopoietin growth factor receptor family, a family characterized by a common structural design of the extracellular domain, including four conserved C residues in the N-terminal portion and a WSXWS motif (SEQ ID NO:1) close to the transmembrane region. See Bazan Proc. Natl. Acad. Sci. USA 87:6934-6938 (1990). Evidence that this receptor plays a functional role in hematopoiesis includes observations that its expression is restricted to spleen, bone marrow, or fetal liver in mice (see Souyri et al. Cell 63:1137-1147 (1990)) and to megakaryocytes, platelets, and CD34$^+$ cells in humans (see Methia et al. Blood 82:1395-1401 (1993)). Some workers postulate that the receptor functions as a homodimer, similar to the situation with the receptors for G-CSF and erythropoietin.

The availability of cloned genes for TPO-R facilitates the search for agonists of this important receptor. The availability of the recombinant receptor protein allows the study of receptor-ligand interaction in a variety of random and semi-random peptide diversity generation systems. These systems are disclosed in U.S. Pat. Nos. 6,251,864, 6,083,913, 6,121,238, 5,932,546, 5,869,451, 6,506,362, and 6,465,430, and in Cwirla et al., Proc. Natl. Acad. Sci. USA 87:6378-6382 (1990), each of the foregoing is incorporated herein by reference.

The morphologically recognizable and functionally capable cells circulating in blood include erythrocytes, neutrophilic, eosinophilic, and basophilic granulocytes, B-, T-, non B-, non T-lymphocytes, and platelets. These mature hematopoietic cells derive from and are replaced, on demand, by morphologically recognizable dividing precursor cells for the respective lineages such as erythroblasts for the erythrocytes series, myeloblasts, promyelocytes and myelocytes for the granulocyte series, and megakaryocytes for the platelets. The precursor cells derive from more primitive cells that can simplistically be divided into two major subgroups: stem cells and progenitor cells (for review, see Broxmeyer, H. E., 1983, "Colony Assays of Hematopoietic Progenitor Cells and Correlations to Clinical Situations," CRC Critical Review in Oncology/Hematology 1:227-257).

The definitions of stem and progenitor cells are operational and depend on functional, rather than on morphological, criteria. Stem cells have extensive self-renewal or self-maintenance capacity (Lajtha, Differentiation, 14:23 (1979)), a necessity since absence or depletion of these cells could result in the complete depletion of one or more cell lineages, events that would lead within a short time to disease and death. Some of the stem cells differentiate upon need, but some stem cells produce other stem cells to maintain the pool of these cells. Thus, in addition to maintaining their own kind, pluripotential stem cells are capable of differentiation into several sublines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, Blood Cells, 5:447 (1979)).

A variety of infectious agents, genetic abnormalities and environmental factors can cause a deficiency in one or more hematopoietic cell types. Additionally, chemotherapy and radiation therapy used in the treatment of cancer and certain immunological disorders can cause pancytopenias or combinations of anemia, neutropenia and thrombocytopenia. Thus, the increase or replacement of hematopoietic cells is often crucial to the success of such treatments. (For a general discussion of hematological disorders and their causes, see, e.g., "Hematology" in Scientific American Medicine, E. Rubenstein and D. Federman, eds., Volume 2, Chapter 5, Scientific American, New York (1996)).

The current therapy available for many hematological disorders as well as the destruction of the endogenous hematopoietic cells caused by chemotherapy or radiotherapy is bone marrow transplantation. However, use of bone marrow transplantation is severely restricted since it is extremely rare to have perfectly matched (genetically identical) donors, except in cases where an identical twin is available or where bone marrow cells of a patient in remission are stored in a viable frozen state. Except in such autologous cases, there is an inevitable genetic mismatch of some degree, which entails serious and sometimes lethal complications. These complications are two-fold. First, the patient is usually immunologically incapacitated by drugs beforehand, in order to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of stem cells for hematopoietic reconstitution (Nothdurtt, W., et al., 1977, Scand. J. Haematol. 19:470-481; Sarpel, S. C., et al., 1979, Exp. Hematol. 7:113-120; Ragharachar, A., et al., 1983, J. Cell. Biochem. Suppl. 7A:78; Juttner, C. A., et al., 1985, Brit. J. Haematol. 61:739-745; Abrams, R. A., et al., 1983, J. Cell. Biochem. Suppl. 7A:53; Prummer, O., et al., 1985, Exp. Hematol. 13:891-898). In some studies, promising results have been obtained for patients with various leukemias (Reiffers, J., et al., 1986, Exp. Hematol. 14:312-315; Goldman, J. M., et al., 1980, Br. J. Haematol. 45:223-231; Tilly, H., et al., Jul. 19, 1986, The Lancet, pp. 154-155; see also To, L. B. and Juttner, C. A., 1987, Brit. J. Haematol. 66:285-288, and references cited therein); and with lymphoma (Korbling, M., et al., 1986, Blood 67:529-532). Other studies using peripheral blood, however, have failed to effect reconstitution (Hershko, C., et al., 1979, The Lancet 1:945-947; Ochs, H. D., et al., 1981, Pediatr. Res. 15:601). Studies have also investigated the use of fetal liver cells transplantation (Cain, G. R., et al., 1986, Transplantation 41:32-25; Ochs, H. D., et al., 1981, Pediatr. Res. 15:601; Paige, C. J., et al., 1981, J. Exp. Med. 153:154-165; Touraine, J. L., 1980, Excerpta Med. 514:277; Touraine, J. L., 1983, Birth Defects 19:139; see also Good, R. A., et al., 1983, Cellular Immunol. 82:44-45 and references cited therein) or neonatal spleen cell transplantation (Yunis, E. J., et al., 1974, Proc. Natl. Acad. Sci. U.S.A. 72:4100) as stem cell sources for hematopoietic reconstitution. Cells of neonatal thymus have also been transplanted in immune reconstitution experiments (Vickery, A. C., et al., 1983, J. Parasitol. 69(3):478-485; Hirokawa, K., et al., 1982, Clin. Immunol. Immunopathol. 22:297-304).

Clearly, there is a tremendous need for methods of expanding blood cells in vitro or therapies, which increase the production of hematopoietic cells in vivo.

Anemia, which is defined as a reduction in the hemoglobin concentration of the blood, is usually associated with a reduction of total circulating red cell mass. Regardless of the cause, anemia decreases the oxygen-carrying capacity of the blood, and when severe enough, causes clinical symptoms and signs.

Clinically, anemia is characterized by pallor of the skin and mucus membranes, and by manifestations of hypoxia, most commonly weakness, fatigue, lethargy, or dizziness. Myocardial hypoxia may produce hyperdynamic circulation with an increase in heart rate and stroke volume. Ejection type flow murmurs may develop, and if the anemia is severe enough, cardiac failure may ensue.

Anemias are generally classified in one of two ways: either by etiological classification (based on the cause) or by morphologic classification (based on changes in shape and size). Etiological classification is more commonly employed.

Alloimmune hemolytic anemia occurs when the antibody of one individual reacts with red blood cells (RBC) of another. Alloimmune hemolytic anemia typically occurs following transfusion of ABO incompatible blood and rhesus disease of the newborn. It also can occur following allogenic transplantation. (Hoffbrand, A. V. in Essential Hematology, 3rd. ed., Blackwell Scientific Publications, 1993, p. 90).

The administration of certain drugs can cause transient drug induced anemia. This can occur by three mechanisms: 1) antibody directed against a drug-red cell membrane complex (e.g., penicillin or cephalothin); 2) deposition of complement via drug-protein (antigen)-antibody complex onto the red cell surface (e.g., quinidine or chloropropamide); or 3) an autoimmune hemolytic anemia in which the role of the drug is unknown (e.g., methyl dopa). In each case, the anemia disappears only after the drug is discontinued (however, with methyl dopa, the antibodies may persist for many months). (Hoffbrand, A. V. in Essential Hematology, 3rd. ed., Blackwell Scientific Publications, 1993, p. 90-1).

Aplastic anemia is defined as pancytopenia (anemia, leucopenia, and thrombocytopenia) resulting from aplasia of the bone marrow. It is classified into primary types: a congenital form (Fanconi anemia) and an acquired form with no obvious precipitating cause (idiopathic). Secondary causes may result from a variety of industrial, iatrogenic and infectious causes. The underlying cause appears to be a substantial reduction in the number of hemopoietic pluripotential stem cells and a defect in the remaining stem cells or an immune reaction against them making them unable to divide and differentiate sufficiently to populate the bone marrow. (Hoffbrand, A. V. in Essential Hematology, 3rd. ed., Blackwell Scientific Publications, 1993, p. 121). Suppresser T-cells as well as immunoglobulins that inhibit erythropoietin or block differentiation of hemopoietic stem cells in vitro have been demonstrated in some cases. (Andreoli, T. in Essentials of Medicine, W. B. Saunders, 1986, p. 349).

Neelis et al., Blood, 90(1):58-63 (1997), discloses that human recombinant TPO stimulated red blood cell lineage recovery in rhesus monkeys exposed to 5 Gy total body irradiation (300-kV x-rays), with reticulocyte regeneration being initiated 10 days earlier than in placebo-treated animals. Neelis et al. also discloses improved hemoglobin and hematocrit values than in controls.

Basser et al., Blood, 89(9):3118-3128 (1997), discloses that administration of PEG-rHuMGDF plus filgastrim elevated peripheral blood progenitor cells of patients exposed to carboplatin 600 mg/m$^2$ and cyclophosphamide 1,200 mg/m$^2$.

Papayannopoulou et al., Exp. Hematol., 24(5):660-669 (1996), discloses the effects of EPO and TPO on the in vitro differentiation toward erythropoiesis and thrombopoiesis.

Kaushansky et al., J. Clin. Invest., 96(3):1683-1687 (1995), discloses that TPO acted in synergy with EPO to expand erythroid progenitors. Kaushansky et al., Exp. Hematol., 24(2):265-269 (1996), discloses that TPO expanded BFU-E, CFU-GM and CFU-Mk progenitor cells in myelosuppressed animals.

Anemia is a serious problem, and has lent urgency to the search for a blood growth factor agonist able to prevent the development of anemia, treat anemia, promote the survival of RBC precursors and/or maintain the normal production of red blood cells. The present invention provides such an agonist.

SUMMARY OF THE INVENTION

The present invention is directed to the use of defined low molecular weight peptide compounds in the treatment of anemia. The defined low molecular weight peptide compounds have strong binding properties to the TPO-R, can activate the TPO-R, potentially permit reduced side effects compared to known TPO agonists, and have the ability to stimulate, in vivo and in vitro, the production of red blood cells. The low molecular weight peptide compounds can be in various forms, e.g., monomers, dimers and oligomers and/or can be derivatized with a hydrophilic polymer. Accordingly, such peptide compounds are useful for therapeutic purposes in treating and/or preventing anemia as well as for diagnostic purposes in studying anemia.

Peptide compounds suitable for therapeutic and/or diagnostic purposes have an $IC_{50}$ of about 2 mM or less, and more preferably of 2 nM or less, as determined by, for example, a Baf/3 binding assay (discussed below), wherein a lower $IC_{50}$ correlates to a stronger binding affinity to TPO-R. For pharmaceutical purposes, the peptide compounds preferably have an $IC_{50}$ of no more than about 100 µM, more preferably no more than about 500 nM, more preferably no more than about 100 pm, and more preferably no more than about 5 pm.

Peptide compounds suitable for therapeutic and/or diagnostic purposes have an $EC_{50}$ of about 2 mM or less, and more preferably of 2 nM or less, as determined using well known techniques in well known assays, such as, for example, a Baf/3 binding assay (discussed below), wherein a lower $EC_{50}$ correlates to a stronger binding affinity to TPO-R. For pharmaceutical purposes, the peptide compounds preferably have an $EC_{50}$ of no more than about 100 µM, more preferably no more than about 500 nM, more preferably no more than about 100 pm, and more preferably no more than about 5 pm.

The molecular weight of the peptide compounds range anywhere from about 500 to about 8,000 daltons, more preferably from about 900 to about 2000 daltons. If the peptide compounds are oligomerized, dimerized and/or derivatized with a hydrophilic polymer as described herein, the molecular weight of such peptide will be greater and can range anywhere from about 1500 to about 120,000 daltons, more preferably from about 3,000 to about 80,000 daltons and more preferably from about 30,000 to about 50,000 daltons.

Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc., as described in U.S. Pat. Nos. 5,672,662 and 5,869,451, the entire content of which is hereby incorporated by reference.

When the peptide compounds are derivatized with a hydrophilic polymer, their solubility and circulation half-lives are increased and their immunogenicity is masked. The foregoing can be accomplished with little, if any, diminishment in their binding activity. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have an average molecular weight of about 5,000 daltons, 10,000 daltons and 20,000 daltons.

The peptide compounds of the invention can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 or WO 95/34326, all of which are incorporated by reference in their entirety herein.

In a presently preferred embodiment, the peptide compounds of the present invention are derivatized with polyethylene glycol (PEG). PEG is a linear, water-soluble polymer of ethylene oxide repeating units with two terminal hydroxyl groups. PEGs are classified by their molecular weights, which typically range from about 500 daltons to about 40,000 daltons. In a presently preferred embodiment, the PEGs employed have molecular weights ranging from 5,000 daltons to about 20,000 daltons. PEGs coupled to the peptide compounds of the present invention can be either branched or unbranched. (See, e.g., Monfardini, C., et al., Bioconjugate Chem., 6:62-69 (1995)). PEGs are commercially available from Nektar Therapeutics (San Carlo, Calif.), Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-$NH_2$), monomethoxypolyethylene glycol-tresylate (MePEG-TRES), and monomethoxypolyethylene glycol-imidazolyl-carbonyl (MePEG-IM).

Briefly, in one embodiment, the hydrophilic polymer which is employed, e.g., PEG, is preferably capped at one end by an unreactive group such as a methoxy or ethoxy group. Thereafter, the polymer is activated at the other end by reaction with a suitable activating agent, such as cyanuric halides (e.g., cyanuric chloride, bromide or fluoride), diimadozle, an anhydride reagent (e.g., a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a peptide compound of the present invention to produce a peptide compound derivatized with a polymer. Alternatively, a functional group in the peptide compounds of the invention can be activated for reaction with the polymer, or the two groups can be joined in a concerted coupling reaction using known coupling methods. It will be readily appreciated that the peptide compounds of the invention can be derivatized with PEG using a myriad of other reaction schemes known to and used by those of skill in the art.

When used for diagnostic purposes, the peptide compounds preferably are labeled with a detectable label and, accordingly, peptide compounds without such a label serve as intermediates in the preparation of labeled peptide compounds.

Preferred peptide compounds are those having:

(1) a molecular weight of less than about 5000 daltons, whether monomer, dimer or oligomer, and (2) a binding affinity to TPO-R as expressed by an $IC_{50}$ of no more than about 100 mM, wherein zero or more of the peptidyl [—C(O)NR—] linkages (bonds) have been replaced by a non-peptidyl linkage such as a —$CH_2$-carbamate linkage [—$CH_2$—OC(O)NR—]; a phosphonate linkage; a —$CH_2$-sulfonamide [—$CH_2$—S(O)$_2$NR-] linkage; a urea [—NHC(O)NH—] linkage; a —$CH_2$-secondary amine linkage; or an alkylated peptidyl linkage [—C(O)NR— where $R^6$ is lower alkyl];

peptides wherein the N-terminus is derivatized to a —$NRR^1$ group; to a —NRC(O)R group; to a —NRC(O)OR group; to a —NRS(O)$_2$R group; to a —NHC(O)NHR group where R and $R^1$ are hydrogen or lower alkyl with the proviso that R and $R^1$ are not both hydrogen; to a succinimide group; to a benzyloxycarbonyl-NH—(CBZ-NH—) group; or to a benzyloxycarbonyl-NH— group having from 1 to 3 substituents on the phenyl ring selected from the grout consisting of lower alkyl, lower alkoxy, chloro, and bromo; or peptides wherein the C terminus is derivatized to —C(O)$R^2$ where $R^2$ is selected from the group consisting of lower alkoxy, and —$NR^3R^4$ where $R^3$ and $R^4$ are independently selected from the group consisting of hydrogen and lower alkyl.

It was found that the core peptide compound can comprise a sequence of amino acids (SEQ ID NO:2):

$$X_1 \; X_2 \; X_3 \; X_4 \; X_5 \; X_6 \; X_7$$

where $X_1$ is C, L, M, P, Q, V; $X_2$ is F, K, L, N, Q, R, S, T or V; $X_3$ is C, F, I, L, M, R, S, V or W; $X_4$ is any of the 20 genetically coded L-amino acids; $X_5$ is A, D, E, G, K, M, Q, R, S, T, V or Y; $X_6$ is β-(2-naphthyl)alanine (2-Nal); and $X_7$ is C, G, I, K, L, M, N, R or V.

In a preferred embodiment, the core peptide compound comprises a sequence of amino acids (SEQ ID NO:3):

$$X_8 \; G \; X_1 \; X_2 \; X_3 \; X_4 \; X_5 \; (2\text{-Nal}) \; X_7$$

where $X_1$ to $X_7$ are as defined above; and each $X_8$ residue is independently selected from any of the 20 genetically coded L-amino acids, their stereoisomeric D-amino acids; and non-natural amino acids.

In yet a preferred embodiment, the core peptide compound comprises a sequence of amino acids (SEQ ID NO:4):

$$X_9 \; X_8 \; G \; X_1 \; X_2 \; X_3 \; X_4 \; X_5 \; (2\text{-Nal}) \; X_7$$

where $X_9$ is A, C, E, G, I, L, M, P, R, Q, S, T, or V; and $X_8$ is A, C, D, E, K, L, Q, R, S, T, or V. More preferably, $X_9$ is A or I; and $X_8$ is D, E, or K.

A particularly preferred peptide compound is (SEQ ID NO:5):

$$I \; E \; G \; P \; T \; L \; R \; Q \; (2\text{-Nal}) \; L \; A \; A \; R \; (Sar)$$

where (Sar) is sarcosine.

In another embodiment, the peptide compound is dimerized or oligomerized to increase the affinity and/or activity of the peptide compound. A particularly preferred peptide compound is a 29-mer peptide having two identical 14-mers linked by a lysinamide residue. A particularly preferred peptide compound therefore is (SEQ ID NO:6, also referred to herein as TPO Compound No. 1):

```
I E G P T L R Q (2-Nal) L A A R (Sar)
                                      \
                                       K(NH2)
                                      /
I E G P T L R Q (2-Nal) L A A R (Sar)
```

A more preferred peptide compound is a pegylated version of TPO Compound No. 1. The pegylated form may include a 20,000 MPEG residue covalently linked to each N-terminal isoleucine. The full molecular structure of an example of such a compound is detailed below:

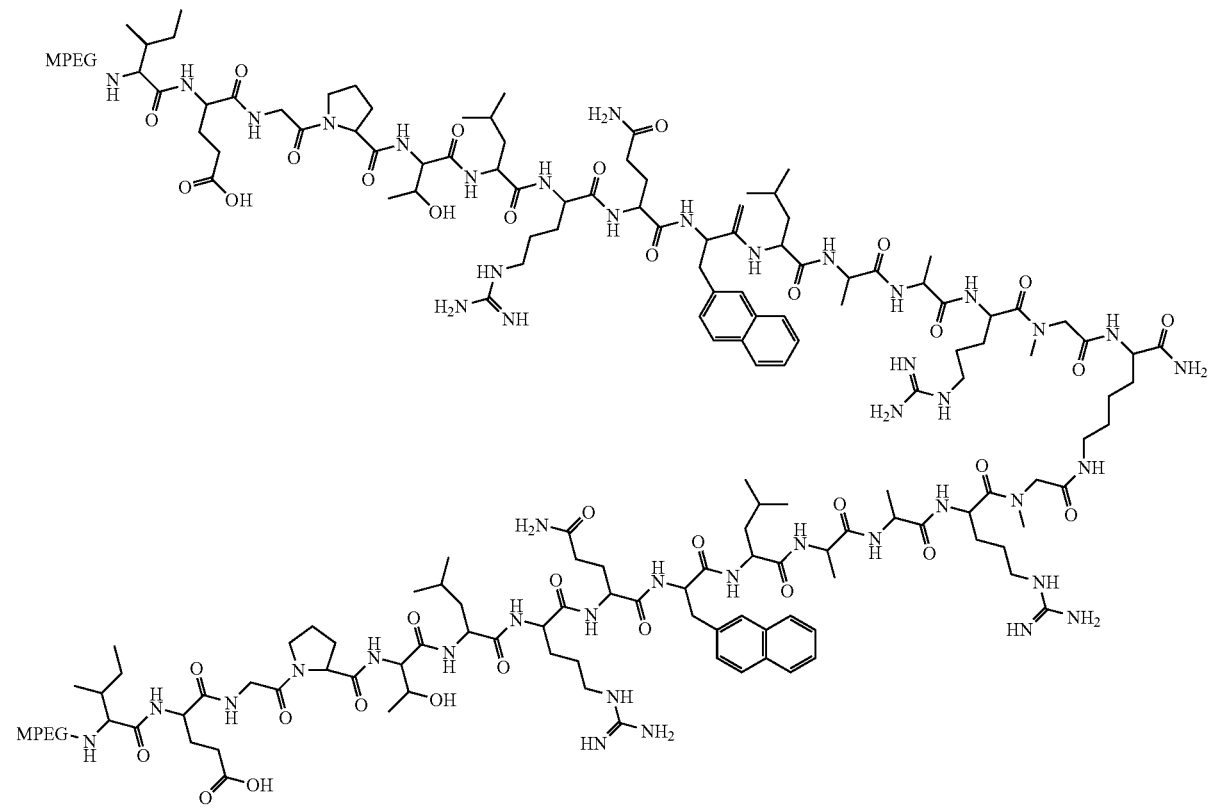

(This compound is referred to herein as PEGylated TPO Compound No. 1). The full chemical name of PEGylated TPO Compound No. 1 is: Methoxypolyethyleneglycol20000-propionyl-L-Isoleucyl-L-Glutamyl-Glycyl-L-Prolyl-L-Threonyl-L-Leucyl-L-Arginyl-L-Glutaminyl-L-2-Naphthylalanyl-L-Leucyl-L-Alanyl-L-Alanyl-L-Arginyl-Sarcosyl-Ne-(methoxypolyethyleneglycol20000-propionyl-L-Isoleucyl-L-Glutamyl-Glycyl-L-Prolyl-L-Threonyl-L-Leucyl-L-Arginyl-L-Glutaminyl-L-2-Naphthylalanyl-L-Leucyl-L-Alanyl-L-Alanyl-L-Arginyl-Sarcosyl-)-Lysinamide.

PEGylated TPO Compound No. 1 is composed of two identical 14 amino acid peptide chains linked by a lysinamide residue and linked on each N-terminal to an approximately 20,000 Dalton molecular weight polyethylene glycol (PEG) chain. The molecular weight of the parent peptide without PEG is 3,295 Daltons and with two PEG chains is approximately 43,295 Daltons. PEGylated TPO Compound No. 1 has an abbreviated molecular structure of (MPEG-Ile-Glu-Gly-Pro-Thr-Leu-Arg-Gln-(2-Nal)-Leu-Ala-Ala-Arg-(Sar))$_2$-Lys-NH$_2$; where (2-Nal) is β-(2-naphthyl)alanine, (Sar) is sarcosine and MPEG is methoxypoly(ethylene glycol) (MW approximately 20,000 Daltons).

One or more peptide compounds, and in particular PEGylated peptide compounds, including pharmaceutically acceptable equivalents thereof (collectively referred to herein as "peptide compounds", "TPO peptide compounds" or "TPO peptide compounds of the invention"), are useful for the prevention and treatment of diseases mediated by TPO, and particularly for treating and/or preventing anemia. Thus, the present invention provides a method for treating and/or preventing anemia, wherein a patient having anemia, or a patient that is expected to develop anemia, receives, or is administered, a therapeutically or a prophylactically effective dose or amount of a peptide compound of the present invention.

The invention also provides for pharmaceutical compositions comprising one or more of the peptide compounds described herein and a physiologically acceptable carrier. These pharmaceutical compositions can be in a variety of forms including oral dosage forms, as well as inhalable powders and solutions and injectable and infusible solutions.

BRIEF DESCRIPTION OF THE FIGURES

FIG. 1 shows the effect of treatment of PEGylated TPO Compound No. 1 on hemoglobin levels as set forth in Example 1.

FIG. 2 shows the effect of treatment of PEGylated TPO Compound No. 1 on red blood cell count as set forth in Example 1.

FIG. 3 shows the effect of treatment of PEGylated TPO Compound No. 1 on hematocrit as set forth in Example 1.

FIG. 4 shows the effect of treatment of PEGylated TPO Compound No. 1 on body weight as set forth in Example 1.

FIG. 5 shows the effect of treatment of PEGylated TPO Compound No. 1 on hemoglobin levels as set forth in Example 2.

FIG. 6 shows the effect of treatment of PEGylated TPO Compound No. 1 on red blood cell count as set forth in Example 2.

FIG. 7 shows the effect of treatment of PEGylated TPO Compound No. 1 on hematocrit as set forth in Example 2.

FIG. 8 shows the effect of treatment of PEGylated TPO Compound No. 1 on body weight as set forth in Example 2.

FIG. 9 shows the effect of treatment of PEGylated TPO Compound No. 1 on hemoglobin levels as set forth in Example 3.

FIG. 10 shows the effect of treatment of PEGylated TPO Compound No. 1 on red blood cell count as set forth in Example 3.

FIG. 11 shows the effect of treatment of PEGylated TPO Compound No. 1 on hematocrit as set forth in Example 3.

FIG. 12 shows the effect of treatment of PEGylated TPO Compound No. 1 on body weight as set forth in Example 3.

FIG. 13 shows the effect of treatment of PEGylated TPO Compound No. 1 on hematocrit as set forth in Example 4.

FIG. 14 shows the effect of treatment of PEGylated TPO Compound No. 1 on body weight as set forth in Example 4.

DESCRIPTION OF SPECIFIC EMBODIMENTS

Figure 15:
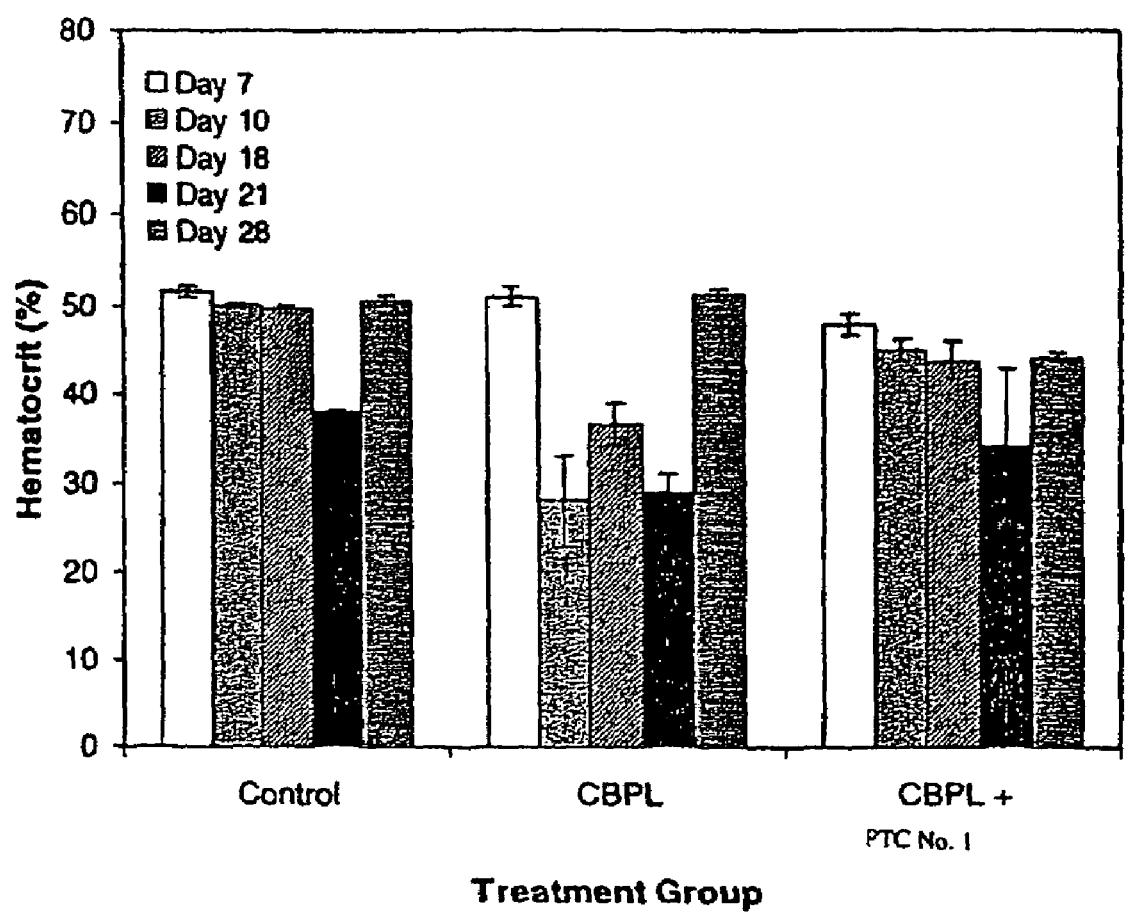
FIG. 15 shows the effect of treatment of PEGylated TPO Compound No. 1 on body weight as set forth in Example 5.

The following definitions are set forth to illustrate and define the meaning and scope of the various terms used to describe the invention herein.

"Agonist" refers to a biologically active ligand which binds to its complementary biologically active receptor and activates the latter either to cause a biological response in the receptor or to enhance preexisting biological activity of the receptor.

"EC$_{50}$" and "50% effective concentration" refer to the concentration of an agonist that produces 50% of the maximum possible effective response for that agonist.

"IC$_{50}$" and "50% inhibitory concentration" refer to the concentration of competing ligand which displaces 50% of the specific binding of the agonist.

"Pharmaceutically acceptable equivalents" includes, without limitation, pharmaceutically acceptable salts, acid addition salts, esters, amides, hydrates, metabolites, prodrugs, and isosteres. Many pharmaceutically acceptable equivalents are expected to have the same or similar in vitro or in vivo activity as the peptide compounds of the invention.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the peptide compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., supra.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., ed., Design of Prodrugs, Elsevier Science Publishers, Amsterdam (1985). These esters are typically formed from the corresponding carboxylic acid and an alcohol. Generally, ester formation can be accomplished via conventional synthetic techniques. (See, e.g., March Advanced Organic Chemistry, 3rd Ed., John Wiley & Sons, New York (1985) p. 1157 and references cited therein, and Mark et al. Encyclopedia of Chemical Technology, John Wiley & Sons, New York (1980)). The alcohol component of the ester will generally comprise (i) a $C_2$-$C_{12}$ aliphatic alcohol that can or can not contain one or more double bonds and can or can not contain branched carbons or (ii) a $C_7$-$C_{12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., Design of Prodrugs, Elsevier Science Publishers, Amsterdam (1985). These amides are typically formed from the corresponding carboxylic acid and an amine. Generally, amide formation can be accomplished via conventional synthetic techniques. (See, e.g., March Advanced Organic Chemistry, 3rd Ed., John Wiley & Sons, New York (1985) p. 1152 and Mark et al. Encyclopedia of Chemical Technology, John Wiley & Sons, New York (1980)). This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, has the ability to rotate the plane of polarized light. However, some pure stereoisomers may have an optical rotation that is so slight that it is undetectable with present instrumentation. The peptide compounds of the instant invention may have one or more asymmetrical carbon atoms and therefore include various stereoisomers. All stereoisomers are included within the scope of the invention.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve an increase in red blood cell production.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Additionally, Bu is Butoxy, Bzl is benzyl, CHA is cyclohexylamine, Ac is acetyl, Me is methyl, Pen is penicillamine, Aib is amino isobutyric acid, Nva is norvaline, Abu is amino butyric acid, Thi is thienylalanine, OBn is O-benzyl, and hyp is hydroxyproline.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. Adv. Drug Res. 15:29 (1986); Veber and Freidinger TINS p. 392 (1985); and Evans et al. J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —$CH_2$ NH—, —$CH_2$S—, —$CH_2$—$CH_2$—, —CH=CH—(cis and trans), —$COCH_2$—, —CH(OH)$CH_2$—, and —$CH_2$ SO—, by methods known in the art and further described in the following references: Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468 (general review); Hudson, D. et al., Int J Pept Prot Res 14:177-185 (1979) (—$CH_2$NH—, $CH_2CH_2$—); Spatola et al. Life Sci 38:1243-1249 (1986) (—$CH_2$—S); Hann J. Chem. Soc Perkin Trans. I 307-314 (1982) (—CH=CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln. EP 45665 CA (1982): 97:39405 (1982) (—CH(OH)$CH_2$—); Holladay et al. Tetrahedron Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2$ NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Labeling of peptidomimetics usually involves covalent attachment of one or more labels, directly or through a spacer (e.g., an amide group); to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference); for example, by adding internal cysteine residues capable of forming intramolecular disulfide bridges which cyclize the peptide.

"Detectable label" refers to materials, which when covalently attached to the peptide compounds of this invention, permit detection of the peptide compound in vivo in the patient to whom the peptide compound has been administered. Suitable detectable labels are well known in the art and include, by way of example, radioisotopes, fluorescent labels (e.g., fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide compound is accomplished by conventional methods well known in the art. For example, when the $^{125}$I radioisotope is employed as the detectable label, covalent attachment of $^{125}$I to the peptide compound can be achieved by incorporating the amino acid tyrosine into the peptide compound and then iodinating the peptide compound. Likewise, $^{32}$P can be incorporated onto the peptide compound as a phosphate moiety through, for example, a hydroxyl group on the peptide compound using conventional chemistry.

The present invention provides peptide compounds that bind to and activate the TPO-R or otherwise behave as a TPO agonist. These peptide compounds include "lead" peptide compounds and "equivalent" or "derivative" peptide compounds constructed so as to have the same or similar molecular structure or shape as the lead peptide compounds but that differ from the lead peptide compounds either with respect to susceptibility to hydrolysis or proteolysis and/or with respect to other biological properties, such as increased affinity for the receptor. The present invention also provides compositions comprising an effective amount of a TPO agonist, and more particularly a peptide compound, that is useful for treating anemia.

The peptide compounds of the invention can also be administered to warm blooded-animals, including humans, to activate the TPO-R in vivo. Thus, the present invention encompasses methods for therapeutic treatment of anemia that comprise administering a peptide compound of the invention in amounts sufficient to mimic the effect of TPO on TPO-R in vivo.

The activity of the peptide compounds of the present invention can be evaluated either in vitro or in vivo in, for example, one of the numerous models described in McDonald Am. J. of Pediatric Hematology/Oncology 14:8-21 (1992), which is incorporated herein by reference, or the assays disclosed herein.

According to one embodiment, the compositions of the present invention are useful for treating anemia associated with bone marrow transfusions, radiation therapy, or chemotherapy. The peptide compounds typically will be administered prophylactically prior to chemotherapy, radiation therapy, or bone marrow transplant or after such exposure.

Accordingly, the present invention also provides pharmaceutical compositions comprising, as an active ingredient, at least one of the peptide compounds of the invention in association with a pharmaceutical carrier or diluent. The peptide compounds of this invention can be administered by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration. See, e.g., Bernstein et al. PCT Patent Publication No. WO 93/25221; Pitt et al. PCT Patent Publication No. WO 94/17784; and Pitt et al. European Patent Application 613, 683, each of which is incorporated herein by reference.

Solid dosage forms for oral administration include capsules, tablets, pills, powders, and granules. In such solid dosage forms, the active peptide compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water or saline. Besides such inert diluents, compositions can also include adjuvants, such as wetting agents, emulsifying and suspending agents, and sweetening, flavoring, and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well Known in the art.

The compositions of the invention can also be microencapsulated by, for example, the method of Tice and Bibi (in Treatise on Controlled Drug Delivery, ed. A. Kydonieus, Marcel Dekker, N.Y. (1992), pp. 315-339).

The compositions containing the peptide compound can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose". Amounts effective for this use will depend on the severity of the disease and the weight and general state of the patient.

In prophylactic applications, compositions containing the peptide compounds of the invention are administered to a patient susceptible to-or otherwise at risk of a particular disease. Such an amount is defined to be a "prophylactically effective dose". In this use, the precise amounts again depend on the patient's state of health and weight.

The quantities of the TPO agonist necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), Goodman and Gilman's: The Pharmacological Basis of Therapeutics, 8th ed., Pergamon Press (1990); and Remington's Pharmaceutical Sciences, 7th ed., Mack Publishing Co., Easton, Pa. (1985); each of which is hereby incorporated by reference.

The peptide compounds of this invention are effective in treating anemia when administered at a dosage range of from about 11 g to about 300 µg/kg of body weight per day. The specific dose employed is regulated by the route of administration as well as by the judgment of the attending clinician depending upon factors such as the severity of the condition, the age and general condition of the patient, and the like.

EXAMPLES

Animal Models

The effects of PEGylated TPO Compound No. 1 on mice treated with carboplatin were observed. For all examples herein, a 10 mg/ml stock solution of PEGylated TPO Compound No. 1 was prepared in sterile saline. For mixing, the preparation was placed on a gyratory shaker for 15 mm. at 200 rpm. This method was used to dissolve PEGylated TPO Compound No. 1 without foaming. The stock was filtered using a GV Millex (0.22 µm) filter. Dosing solutions were then prepared from this stock using sterile saline. The stock and dosing solutions were prepared fresh on the day of use.

Example 1

The effect of PEGylated TPO Compound No. 1 on the duration and severity of anemia following treatment of mice with carboplatin as determined by changes in hemoglobin levels, red blood cell count and hematocrit, was observed. For this study, increasing amounts of PEGylated TPO Compound No. 1 were administered to mice one day following a carboplatin dose to characterize a possible dose-dependent effect on various red blood cell parameters.

The groups of mice were treated with either carboplatin or vehicle (Phosphate Buffered Saline, PBS) by intraperitoneal administration on Days −2 and −1 as delineated below. The optimal dose of carboplatin used to induce thrombocytopenia in the BALB/c mouse strain was previously determined to be a fractionated total dose of 120 mg/kg given as two consecutive daily injections (i.e., 2×60 mg/kg). One day following the second dose of carboplatin, groups of mice were treated with PEGylated TPO Compound No. 1 or vehicle (sterile saline, SS, preservative-free 0.90% sodium chloride) by IV (bolus) injection as delineated in Table 1. The dose was administered on a per-weight basis (100 µl/10 g body weight).

TABLE 1

| | | Treatment Groups: | | | |
|---|---|---|---|---|---|
| Gp | N | Pretreatment (ip), Day −2 & −1 | Test Article | Dose (iv) Day 0 | Blood Collection |
| 1 | 10 | Vehicle (PBS) | Vehicle (SS) | Sham | Eut 5 mice on Day 5 & 11 |
| 2 | 20 | Carboplatin | Vehicle (SS) | Sham | Eut 5 mice on Days 5, 7, 9 & 11 |
| 3 | 20 | Carboplatin | PEGylated TPO Compound No. 1 | 300 µg/kg | Eut 5 mice on Days 5, 7, 9 & 11 |
| 4 | 20 | Carboplatin | PEGylated TPO Compound No. 1 | 1000 µg/kg | Eut 5 mice on Days 5, 7, 9 & 11 |
| 5 | 20 | Carboplatin | PEGylated TPO Compound No. 1 | 3000 µg/kg | Eut 5 mice on Days 5, 7, 9 & 11 |

Gp = Group;
Eut = Euthanized

On Days 5, 7, 9 and 11, five mice in each test group were weighed and then euthanised using $CO_2$-asphyxiation and exsanguinations via cardiac puncture. The blood samples were transferred to separate EDTA (lavender-top) microcontainers for hematologic evaluation. Groups of control mice (5) were processed on Days 5 and 11. Results are shown in FIGS. 1-4. The data are presented graphically as group means +SEM.

Treatment of mice with carboplatin alone caused about a 20% decrease in hemoglobin levels in the mice by Day 11. This decrease was inhibited by treatment with all doses of PEGylated TPO Compound No. 1. Minor decreases in RBC count and hematocrit were also associated with carboplatin treatment, an effect that was inhibited by treatment with PEGylated TPO Compound No. 1; however statistical evaluation of this effect was not conducted. Mice in all groups treated with carboplatin alone or carboplatin plus the various doses of PEGylated TPO Compound No. 1 experienced weight loss on Days 5, 7 and 9 relative to body weight measurements collected on Day 0. Analysis of the body weight measurements in a subset of mice over the 11-Day study period suggests that carboplatin treatment alone caused the observed decrease in body weights and that PEGylated TPO Compound No. 1 enhanced the recovery of the lost body weight at all doses tested.

Mice treated with carboplatin alone began to exhibit altered appearance and behavior by Day 5. Some of the mice assumed a hunched position and appeared flaccid. Many mice also had soiled anogenital areas. Treatment with PEGylated TPO Compound No. 1 decreased the onset, frequency and severity of these signs in manner that appeared to be dose-dependent.

Example 2

The possibility that PEGylated TPO Compound No. 1 may sensitize bone marrow hematopoietic stem cells of mice to the toxic effects of carboplatin treatment was examined. For this study, a dose of PEGylated TPO Compound No. 1 was administered to the mice seven days prior to the carboplatin dose or immediately after carboplatin treatment. An additional group was treated with PEGylated TPO Compound No. 1 both prior to and after carboplatin administration. The effect of these dosing regimens on hematological parameters was also observed.

The groups of mice were treated with either carboplatin or vehicle (Phosphate Buffered Saline, PBS) by ip administration on Days 7 and 8 as delineated below. The optimal dose of carboplatin used to induce thrombocytopenia in the BALB/c mouse strain was previously determined to be a fractionated total dose of 120 mg/kg given as two consecutive daily injections (i.e., 2×60 mg/kg). Seven days prior to the first carboplatin dose or one (1) hour after the second dose of carboplatin, groups of mice were treated with PEGylated TPO Compound No. 1 (300 µg/kg) or vehicle (sterile saline, SS, preservative-free 0.9% sodium chloride) by IV (bolus) injection as delineated in Table 2. An additional group was treated with PEGylated TPO Compound No. 1 both before (Day 0) and after (Day 8, t=1 h) the carboplatin dose. All dosing was performed on a per-weight basis (100 µl/10 g body weight).

on Day 0; however, the administration of PEGylated TPO Compound No. 1 on Day 0 (only) failed to affect carboplatin-induced changes in these erythrocyte parameters.

All mice in the control group experienced normal weight gain between Days 7 and 26, while all mice treated with carboplatin alone lost small amounts of body weight (averaging approximately 4%) during the same time period. Mice in all groups that were treated with carboplatin and various co-treatments with PEGylated TPO Compound No. 1 either maintained body weight or experienced normal weight gain between Days 7 and 26. Analysis of the body weight measurements over the study period suggests that carboplatin treatment was the major contributor to the observed decreases in body weights and that co-treatment with PEGylated TPO Compound No. 1 prevented this weight loss, however a statistical analysis was not conducted. Differences in body weights observed between Day 7 (prior to dosing with carboplatin) and Day 26 (study termination) are presented in FIG. 8.

All mice in the control groups appeared normal throughout the study period. Mice treated with carboplatin alone began to exhibit altered appearance and behavior as early as Day 12 with frequent signs of hunching and appearing unkempt. Many mice receiving carboplatin (without or with PEGylated TPO Compound No. 1 treatment) assumed a hunched position and appeared unkempt during the latter half of the study period. Treatment with PEGylated TPO Compound No. 1 on Day 8 without or with additional treatment on Day 0 appeared to delay the onset of these signs and treatment on Days 0 and 8 decreased the severity and duration as well; however a

TABLE 2

Study Design:

| Gp | N | Dose (iv) Day 0 | Carboplatin (CBPL) [60 mg/kg, q2d], (ip), Day 7 & 8 | Dose (iv) Day 8 (1 h after $2^{nd}$ CBPL dose) | Blood Collection Eut 5 mice on Days |
|---|---|---|---|---|---|
| 1 | 10 | Vehicle (*SS) | Vehicle (PBS) | Vehicle (*SS) | 14 & 26 |
| 2 | 20 | Vehicle (*SS) | Carboplatin | Vehicle (*SS) | 14, 18, 22 & 26 |
| 3 | 20 | PEGylated TPO Compound No. 1 300 µg/kg | Carboplatin | Vehicle (*SS) | 14, 18, 22 & 26 |
| 4 | 20 | Vehicle (*SS) | Carboplatin | PEGylated TPO Compound No. 1 300 µg/kg | 14, 18, 22 & 26 |
| 5 | 20 | PEGylated TPO Compound No. 1 300 µg/kg | Carboplatin | PEGylated TPO Compound No. 1 300 µg/kg | 14, 18, 22 & 26 |

On Days 14, 18, 22 and 26, five mice in each test group were weighed and then euthanised using $CO_2$-asphyxiation and exsanguination via cardiac puncture. The blood samples were transferred to separate EDTA (lavender-top) microcontainers for hematological evaluation. Groups of control mice (5) were processed on Days 14 and 26. Results are shown in FIGS. 5-8. The data are presented graphically as group means +SEM.

Treatment of mice with carboplatin alone caused decreases (approx. 18%) in hemoglobin levels, RBC counts and hematocrits in the surviving mice by Days 18 and 22 compared to control groups. These decreases were prevented by the administration of PEGylated TPO Compound No. 1 on Day 8 (1 hour after the second carboplatin treatment) without or with an additional dose of PEGylated TPO Compound No. 1 detailed analysis of the effects of treatment on systemic observations was not conducted.

Example 3

The effect of PEGylated TPO Compound No. 1 on the duration and severity of anemia following dosing regimens in which PEGylated TPO Compound No. 1 is administered at various times following the carboplatin treatment was observed. For this study, an amount of PEGylated TPO Compound No. 1 was administered to mice, one (1) hour, one (1) day or four (4) days following a carboplatin dose.

The groups of mice were treated with either carboplatin or vehicle (Phosphate Buffered Saline, PBS) by ip administration on Days −1 and 0 as delineated below. The optimal dose of carboplatin used to induce thrombocytopenia in the BALB/c mouse strain was previously determined to be a fractionated total dose of 120 mg/kg given as two consecutive daily injections (i.e., 2×60 mg/kg). One hour (Day 0), one day (Day 1) or four days (Day 4) following the second dose of carboplatin, groups of mice were treated with PEGylated TPO Compound No. 1 (300 μg/kg) or vehicle (sterile saline, SS, preservative-free 0.9% sodium chloride) by IV (bolus) injection as delineated in Table 3. The dose was administered on a per-weight basis (100 μl/10 g body weight).

TABLE 3

Treatment Groups:

| Gp | N | Pretreatment [2 × 60 mg/kg], (ip), Day −1 & 0 | Test Article | Dose (iv) | Blood Collection Eut 5 mice on |
|---|---|---|---|---|---|
| 1 | 10 | Vehicle (PBS) | Vehicle (SS) | Sham | Days 6 & 12 |
| 2 | 20 | Carboplatin | Vehicle (SS) | Sham | Days 6, 8, 10 & 12 |
| 3 | 20 | Carboplatin | PEGylated TPO Compound No. 1 | 300 μg/kg, Day 0 | Days 6, 8, 10 & 12 |
| 4 | 20 | Carboplatin | PEGylated TPO Compound No. 1 | 300 μg/kg, Day 1 | Days 6, 8, 10 & 12 |
| 5 | 20 | Carboplatin | PEGylated TPO Compound No. 1 | 300 μg/kg, Day 4 | Days 6, 8, 10 & 12 |

Gp = Group;
Eut = Euthanized

On Days 6, 8, 10 & 12, five mice in each test group were weighed and then euthanised using $CO_2$-asphyxiation and exsanguinations via cardiac puncture. The blood samples were transferred to separate EDTA (lavender-top) microcontainers for hematological evaluation. Groups of control mice (5) were processed on Days 6 & 12. Results are shown in FIGS. 9-12. The data are presented graphically as group means +SEM.

Treatment of mice with carboplatin alone caused dramatic decreases (approx. 47%) in hemoglobin levels, RBC counts and hematocrits in the surviving mice (2 mice) by Day 12 compared to control groups. These decreases were prevented by the administration of PEGylated TPO Compound No. 1 on Day 0 (1 hour after carboplatin treatment) and on Day 1; however, the administration of PEGylated TPO Compound No. 1 on Day 4 failed to affect carboplatin-induced changes in these erythrocyte parameters.

Mice in all groups treated with carboplatin alone or carboplatin plus the various doses of PEGylated TPO Compound No. 1 experienced weight loss on Days 6, 8, 10 and 12 relative to body weight measurements collected on Day-1. Analysis of the body weight measurements over the study period suggests that carboplatin was the major contributor to the observed decreases in body weights. The administration of PEGylated TPO Compound No. 1 on Days 0, Day 1 or Day 4 did not appear to affect the weight loss associated with carboplatin treatment, however a statistical analysis was not conducted. Decreases in body weights observed between Day-1 and Day 10 are presented in FIG. 11).

All mice in the control groups appeared normal throughout the study period. Mice treated with carboplatin alone began to exhibit altered appearance and behavior as early as Day 2 with frequent signs of hunching and appearing flaccid. Many mice receiving carboplatin (without or with PEGylated TPO Compound No. 1 treatment) assumed a hunched position and appeared flaccid in the latter half of the study period. Some of these mice also had soiled anogenital areas. Other infrequent signs included appearing emaciated, having sagging eyelids and exhibiting an abnormal gate. Treatment with PEGylated TPO Compound No. 1 did not appear to have a dramatic effect on the onset, frequency or the severity of these signs, however a detailed analysis was not conducted.

Prevention of carboplatin-induced anemia is observed when animals are dosed with PEGylated TPO Compound No. 1 within 24 hours of chemotherapy. This data suggests that PEGylated TPO Compound No. 1 has myeloprotective effects that are not limited to the megakaryocyte lineage.

Example 4

The ability of PEGylated TPO Compound No. 1 to function as a survival factor for megakaryocyte and erythrocyte lineages in carboplatin-treated mice as determined by changes in hematological parameters was observed. In previous studies, doses of PEGylated TPO Compound No. 1 as low as 300 μg/kg were found to prevent the anemia induced by carboplatin. In this study, the effect of lower doses of PEGylated TPO Compound No. 1 (i.e., 30, 100 and 300 μg/kg) on the survival of erythrocyte lineages was examined to characterize the dose-response for this effect.

The groups of mice were treated with either carboplatin or vehicle (Phosphate Buffered Saline, PBS) by ip administration on Days −1 and 0 as delineated below. The optimal dose of carboplatin used to induce thrombocytopenia in the BALB/c mouse strain was previously determined to be a fractionated total dose of 120 mg/kg given as two consecutive daily injections (i.e., 2×60 mg/kg). Approximately one hour following the second dose of carboplatin, groups of mice were treated with PEGylated TPO Compound No. 1 or vehicle (sterile saline, SS, preservative-free 0.9% sodium chloride) by IV (bolus) injection as delineated in Table 4. The dose was administered on a per-weight basis (100 μl/10 g body weight).

TABLE 4

Treatment Groups:

| Gp | N | Pretreatment (ip), Day −1 & 0 | Test Article | Dose (iv) Day 0 | Blood Collection |
|---|---|---|---|---|---|
| 1 | 10 | Vehicle (PBS) | Vehicle (SS) | Sham | Eut 5 mice on Day 6 & 12 |
| 2 | 15 | Carboplatin | Vehicle (SS) | Sham | Eut 5 mice on Days 6, 8 & 12 |
| 3 | 15 | Carboplatin | PEGylated TPO Compound No. 1 | 30 µg/kg | Eut 5 mice on Days 6, 8 & 12 |
| 4 | 15 | Carboplatin | PEGylated TPO Compound No. 1 | 100 µg/kg | Eut 5 mice on Days 6, 8 & 12 |
| 5 | 15 | Carboplatin | PEGylated TPO Compound No. 1 | 300 µg/kg | Eut 5 mice on Days 6, 8 & 12 |

Gp = Group;
Eut = Euthanized

On Days 6, 8 and 12, five mice in each test group were weighed and then euthanised using $CO_2$-asphyxiation and exsanguinations via cardiac puncture. The blood samples were transferred to separate EDTA (lavender-top) microcontainers for hematologic evaluation. Groups of control mice (5) were processed on Days 6 & 12. Results are shown in FIGS. 13-14.

Treatment of mice with carboplatin alone caused a greater than 25% decrease in hemoglobin levels in the mice by Day 12. This decrease was totally inhibited by treatment with all doses of PEGylated TPO Compound No. 1. PEGylated TPO Compound No. 1 also effectively inhibited the decreases in RBC counts and hematocrit that were induced by carboplatin treatment.

Essentially all of the mice in all groups treated with either carboplatin alone or carboplatin plus the various doses of PEGylated TPO Compound No. 1 experienced weight loss on Days 6, 8 and 12 relative to body weight measurements collected on Day −1. Analysis of the body weight measurements over the 13-Day study period indicates that carboplatin treatment alone caused the observed decrease in body weights. PEGylated TPO Compound No. 1 did not appear to affect weight loss or recovery in this study.

Mice treated with carboplatin alone began to exhibit altered appearance and behavior by Day 4. Some of the mice assumed a hunched position and appeared unkempt. Many mice also had soft stool. Few animals appeared flaccid and few presented with blood in stool. Treatment with PEGylated TPO Compound No. 1 decreased the onset, frequency and severity of these signs in manner that appeared to be dose-dependent.

PEGylated TPO Compound No. 1 functioned to maintain the survival of erythrocyte lineages in carboplatin-treated mice as determined by peripheral blood platelet counts and other hematological parameters. All doses of PEGylated TPO Compound No. 1 were found to completely prevent the anemia induced by carboplatin on Day 12. These results suggest a differential sensitivity/responsiveness of the megakaryocyte and erythrocyte lineages to the "survival maintenance" effects of PEGylated TPO Compound No. 1.

Example 5

Groups of mice were treated with two rounds of the chemotherapeutic agent (carboplatin) ten days apart, with each round consisting of two consecutive days of carboplatin (i.e., 70 mg/kg/day administered on Days −1 & 0 and Days 10 & 11) as delineated below. The dose of carboplatin utilized for these survival studies exceeded the maximal tolerated dose for mice (i.e., 120 mg/kg; administered as 60 mg/kg/day on 2 consecutive days). One hour following the second dose of carboplatin in each round (i.e., Day 0 and 11) mice were treated with PEGylated TPO Compound No. 1 (100 µg/kg) or vehicle (sterile saline, SS, preservative-free 0.9% sodium chloride) by IV (bolus) injection as delineated below. The dose was administered on a per weight basis (100 µl/10 g body weight).

TABLE 4a

Study Design:

| Gp | N | Pretreatment (ip), Day −1 & 0, Day 10 & 11 | Test Article 100 ug/kg (iv) | Dose (iv) ~1 h after 2ndCBPL dose for ea. cycle | Blood Collection/ Analysis Eut 5 mice on |
|---|---|---|---|---|---|
| 1 | 25 | Vehicle (PBS) | Vehicle (*SS) | Sham, Day 0 & 11 | Days 7, 10, 18, 21 & 28 |
| 2 | 25 | Carboplatin (70 mg/kg) | Vehicle (*SS) | Sham, Day 0 & 11 | Days 7, 10, 18, 21 & 28 |
| 3 | 25 | Carboplatin (70 mg/kg) | PEGylated TPO Compound No. 1 | 100 µg/kg, Day 0 & 11 | Days 7, 10, 18, 21 & 28 |

On days 7, 10, 18, 21 and 28 five mice in each test group (25 mice/group) then euthanised using $CO_2$-asphyxiation and exsanguinations via cardiac puncture. The blood samples were transferred to separate EDTA (lavender-top) microcontainers for hematological evaluation. Groups of control mice treated with the vehicles alone were processed in the same manner. Results are shown in FIG. 15. Treatment of mice with two rounds of carboplatin resulted in the development of a moderate anemia that was observed between days 10 and 21 while, mice treated with 2 rounds of carboplatin and PEGylated TPO Compound No. 1 maintained hematocrit values throughout this period that were similar to the control group. Interestingly, of the mice not utilized for hematological evaluation, 7 mice in the group treated with carboplatin alone died between days 4 and 18 while only 1 mouse in the group receiving combination therapy expired within the same period, with most of the deaths occurring within the period of anemia. These results suggest that carboplatin-induced anemia may contribute the death of mice receiving high levels of chemotherapy and that PEGylated TPO Compound No. 1 may function to increase the survival of the mice by preventing the development of the anemia.

Example 6

For mechanistic studies, groups of mice were treated with vehicle or increasing amounts of carboplatin (i.e., 60, 70 or 80 mg/kg) for 2 consecutive days (Day −1 & Day 0). Approximately one hour following the second dose of carboplatin, groups of mice were treated with PEGylated TPO Compound No. 1 (100 µg/kg) or vehicle (sterile saline, SS, preservative-free 0.9% sodium chloride) by IV (bolus) injection as delineated in Table 5.

TABLE 5

Study Design:

| Gp | N | CBPL dosed Days −1 & 0 (ip) | Treatment (iv), Day 1, 1 h post-CBPL | Blood Collection/ Analysis Eut 3 mice on |
|---|---|---|---|---|
| 1 | 3 | Vehicle (PBS) | Vehicle (*SS) | Day 15 |
| 2 | 3 | Carboplatin (60 mg/kg) | Vehicle (*SS) | Day 15 |
| 3 | 3 | Carboplatin (70 mg/kg) | Vehicle (*SS) | Day 15 |
| 4 | 3 | Carboplatin (80 mg/kg) | Vehicle (*SS) | Day 15 |
| 5 | 3 | Carboplatin (60 mg/kg) | PEGylated TPO Compound No. 1 (100 µg/kg) | Day 15 |
| 6 | 3 | Carboplatin (70 mg/kg) | PEGylated TPO Compound No. 1 (100 µg/kg) | Day 15 |
| 7 | 3 | Carboplatin (80 mg/kg) | PEGylated TPO Compound No. 1 (100 µg/kg) | Day 15 |

On Day 15, the mice in all treatment groups were euthanised using $CO_2$-asphyxiation and exsanguinations via cardiac puncture. The blood samples were transferred to separate EDTA (lavender-top) microtainers for hematologic evaluation. In addition, several organs (including the brains) of control mice and mice treated with 2×70 mg/kg carboplatin without and with co-treatment with PEGylated TPO Compound No. 1 were isolated and processed for histological examination. Sections of these tissues were processed immunohistochemically for fibrinogen/fibrin.

Treatment of mice with increasing amounts of carboplatin alone caused a dramatic drop in the number of platelets in mice receiving 2×70 mg/kg on Day 15 and a dose-dependent decrease in hematocrit (HCT) in mice treated with the 60 and 70 mg/kg carboplatin (alone). These decreases in platelet and RBC counts induced by the carboplatin were totally inhibited by treatment with the PEGylated TPO Compound No. 1. It should be noted that all of the mice treated with 2×80 mg/kg carboplatin (alone) were either found dead or were euthanized (moribund) prior to study termination. Interestingly, all of the mice treated with 2×80 mg/kg carboplatin and PEGylated TPO Compound No. 1 survived until the scheduled study termination and did not exhibit thrombocytopenia or anemia on Day 15.

Histological evaluation of the brains of control mice exhibited small blood vessels that appeared normal. Many of the vessels contained red blood cells and exhibited a dim stain for fibrinogen. Dim, intravascular staining for fibrinogen/fibrin is expected in these control mice since fibrinogen is a normal component of plasma. Brain sections from mice treated with carboplatin alone (2×70 mg/kg) contained small blood vessels that were totally occluded by material staining intensely positive for fibrinogen/fibrin. These microthrombi were frequently observed in tissue sections from all mice of this dose group. The small vessels in brain sections from mice treated with carboplatin and PEGylated TPO Compound No. 1 appeared normal or exhibited fibrinogen/fibrin staining that was only slightly darker than the control group. A single, microthrombotic event was noted for the entire dose group.

The results of this study indicate that microthrombotic events are induced by chemotherapy and, since microthrombi are thought to contribute to the mechanical lysis of RBCs, it is likely that these vascular events contribute to chemotherapy-induced anemia. In addition, the ability of the PEGylated TPO Compound No. 1 to prevent the development of these thrombotic events may be a component of the mechanism by which this agent prevents the development of the anemia induced by chemotherapy. Lastly, the microthrombotic events may have also contributed to the mortality of animals that received high dose chemotherapy. Therefore, the ability of the PEGylated TPO Compound No. 1 to prevent the development of these thrombotic events may be responsible for the increased survival of the animals that received high dose chemotherapy and the agent.

Figure 18A:
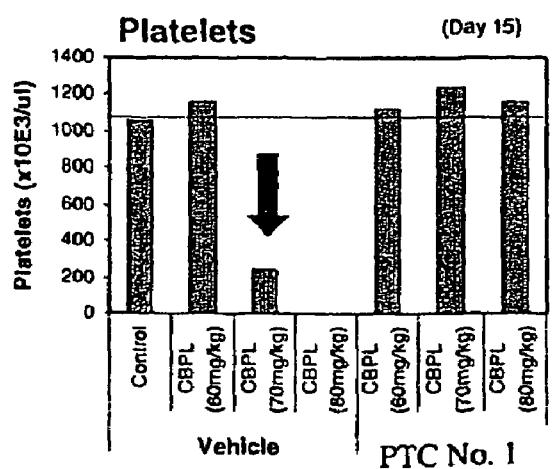
FIG. 18A and FIG. 18B show the effect on platelets (FIG. 18A) and hematocrit (FIG. 18B) of carboplatin treated mice as a result of treatment with PEGylated TPO Compound No. 1 as set forth in Example 6.
Figure 18B:
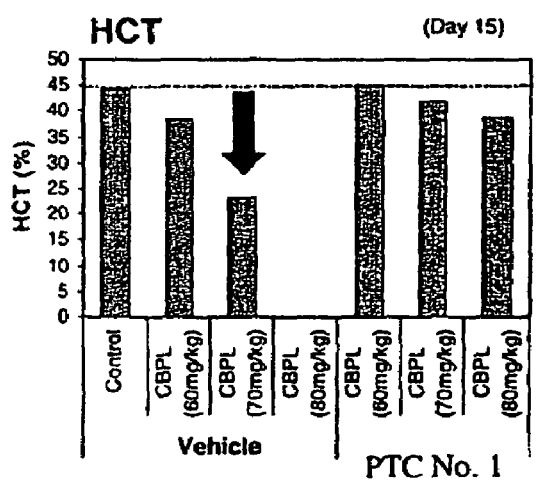

FIG. 18A and FIG. 18B shows the effect of treatment of PEGylated TPO Compound No. 1 on platelets and hematocrit of carboplatin treated mice [as set forth in Example 6].

Figure 19:
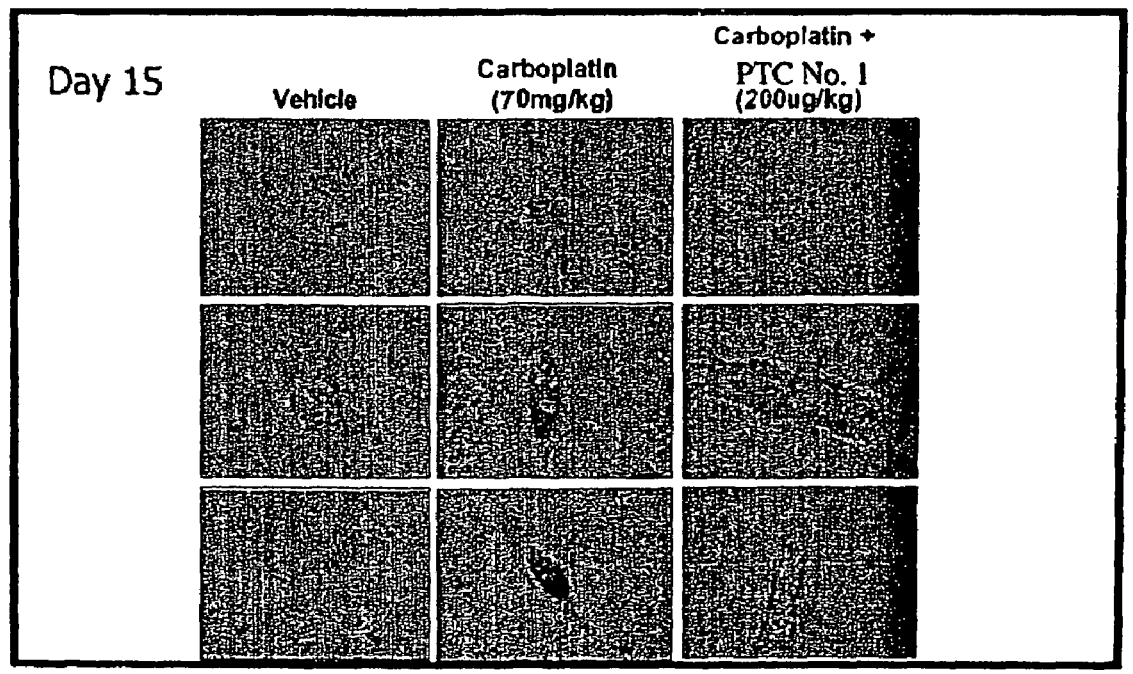
FIG. 19 shows the effect on fibrinogen deposition and blood clots in brain sections from carboplatin treated mice as a result of treatment with PEGylated TPO Compound No. 1 as set forth in Example 6.

FIG. 19 shows that administration of PEGylated TPO Compound No. 1 reduces fibrinogen deposition and blood clots in brain sections from carboplatin treated mice as set forth in Example 6.

Proposed Mechanism of Action

Figure 16:
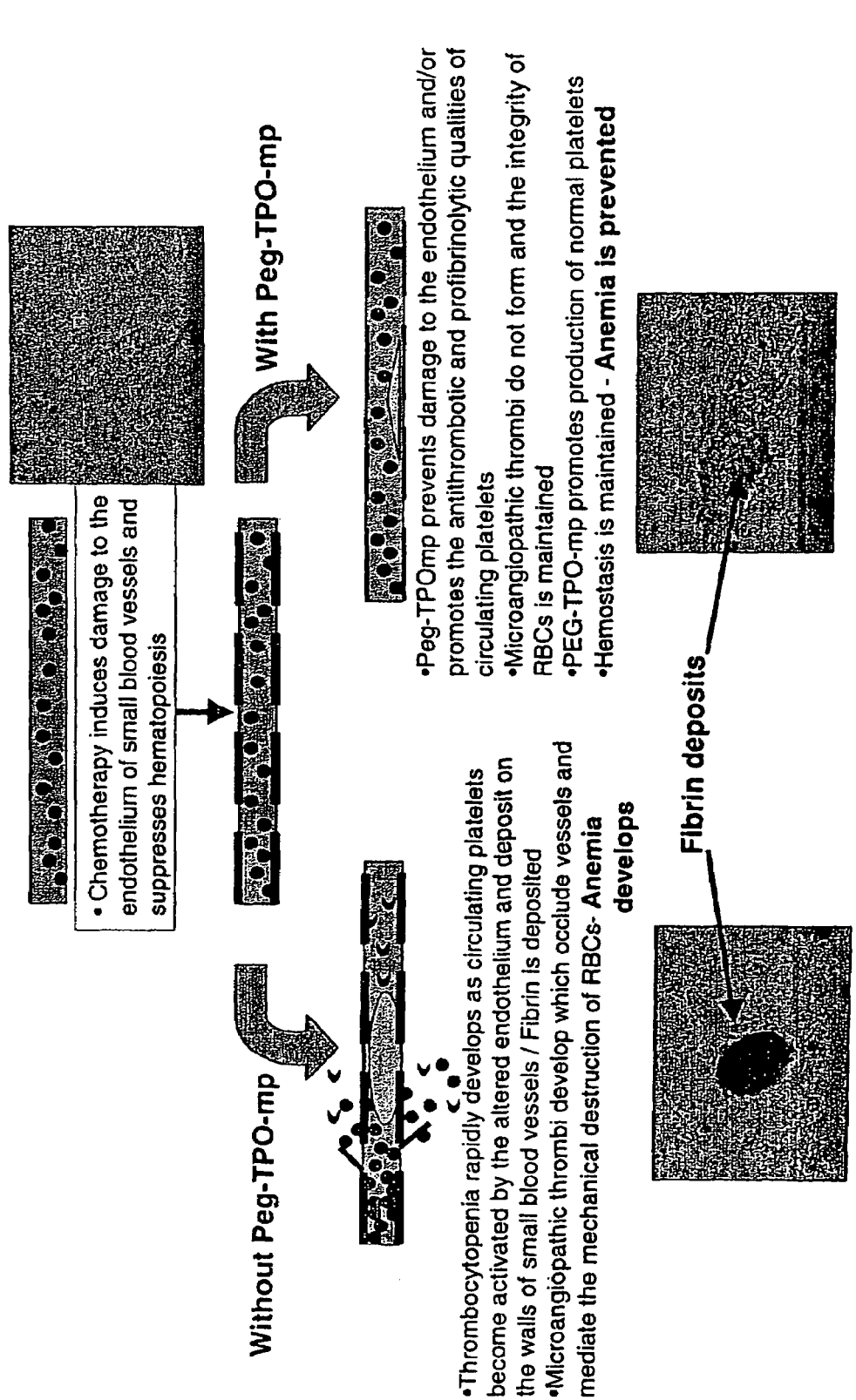
FIG. 16 shows what is believed to be the anti-anemic mechanism of action of PEGylated TPO Compound No. 1.

FIG. 16 shows what is believed to be the mechanism of action of the anti-anemic effects of PEGylated TPO Compound No. 1. As can be seen by FIG. 16, chemotherapy induces damage to the endothelium of small blood vessels and suppresses hematopoiesis. In the absence of PEGylated TPO Compound No. 1, a thrombocytopenia rapidly develops as circulating platelets become activated by the altered endothelium and deposit on the walls of small blood vessels. Altered platelets, produced by the compromised marrow, contribute to this process. The activated platelets induce the deposition of fibrin within the damaged vessels and microangiopathic thrombi develop. These microangiopathic thrombi mediate the mechanical destruction of red blood cells contributing to the development of chemotherapy-induced anemia. Co-treatment with PEGylated TPO Compound No. 1 inhibits chemotherapy-induced damage to the endothelium of blood vessels and/or promotes the antithrombotic and profibrinolytic qualities of circulating platelets. Microangiopathic thrombi do not develop and the structural integrity of red blood cells is maintained. The effect of PEGylated TPO Compound No. 1 on megakaryocyte precursors in the marrow, promotes the production of normal platelets. Hemostasis is maintained and anemia is prevented.

Figure 17:
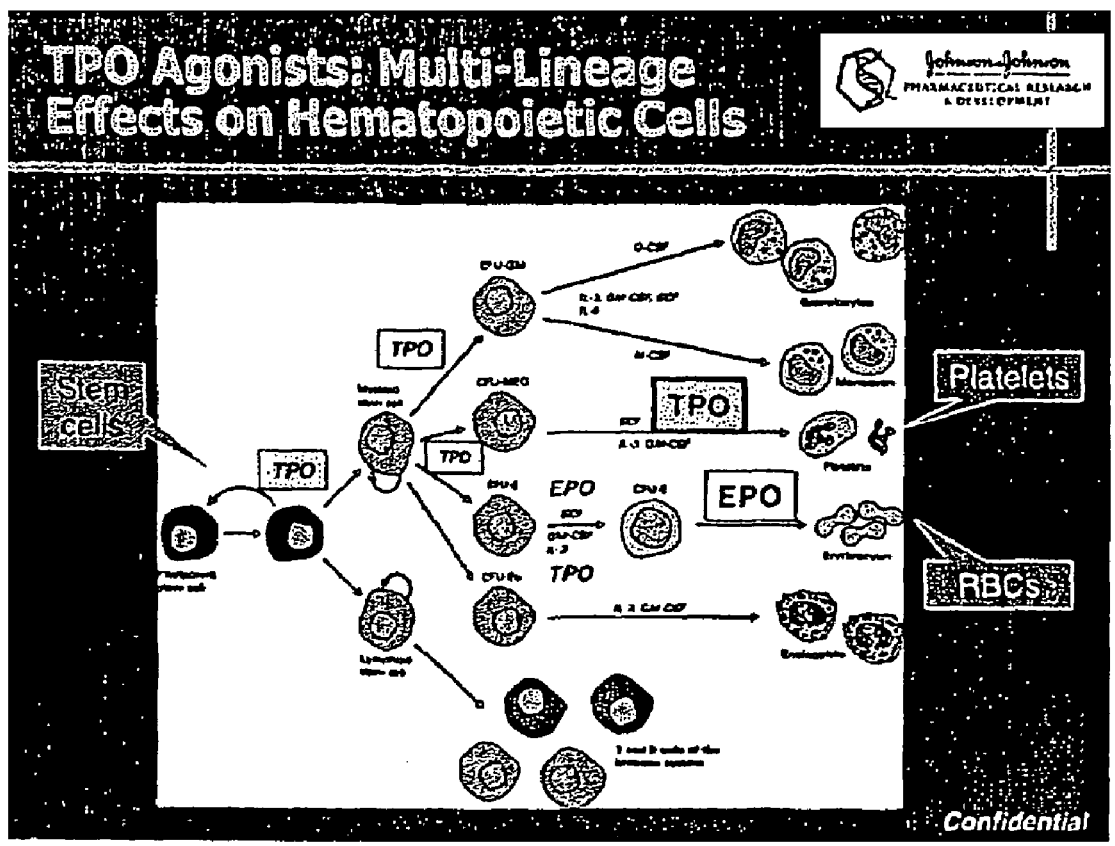
FIG. 17 shows what is believed to be some of the lineage effects on hematopoietic cells of PEGylated TPO Compound No. 1.

FIG. 17 shows what is believed to be some of the lineage effects on hematopoietic cells of PEGylated TPO Compound No. 1.

Example 7

Binding Assay

The activity of the peptide compounds can be determined using standard relative luminescent units assay techniques. The assay employs, e.g., murine cells engineered to stably express the human TPO receptor and a luciferase reporter construct driven by the fos promoter. The assay may be performed as follows: Serum deprived Baf/3 hTPOr fos/lux cells expressing the human TPO receptor, c-mpl (hTPOr), and a luciferase reporter construct are exposed to increasing concentrations of either rhTPO or peptide compound for approximately 18 hours. Cells are then incubated in a medium containing a luciferase substrate and the luminescence of the cells is measured using a luminometer.

Figure 20:
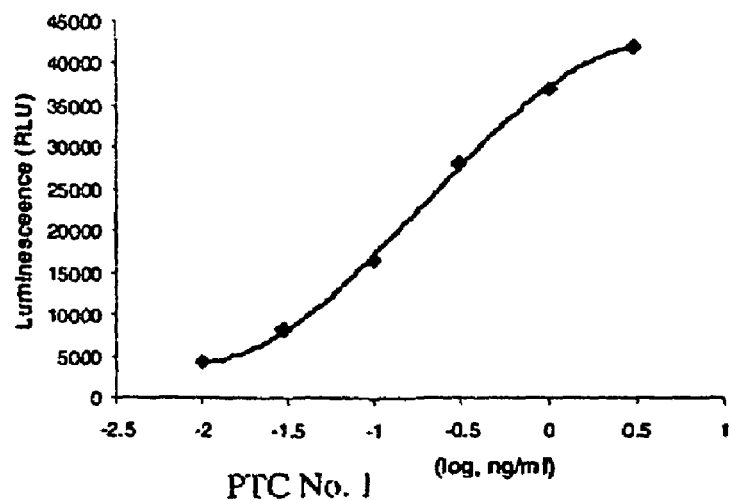
FIG. 20 shows the effect of PEGylated TPO Compound No. 1 on human TPO-R activation in Baf/3 cells as set forth in Example 7.
Figure 21:
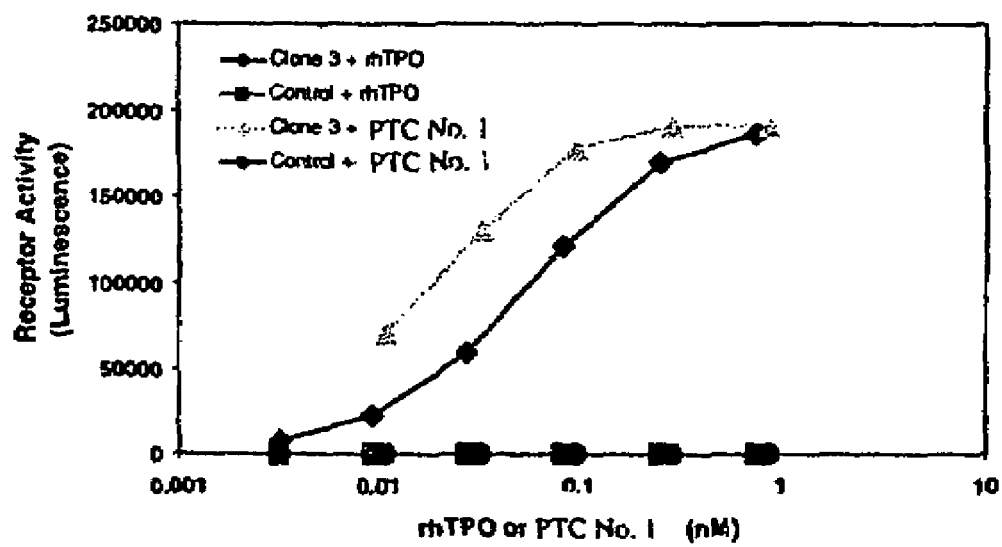
FIG. 21 shows that PEGylated TPO Compound No. 1 activated Baf/3 cells recombinantly expressing human TPO-R in a dose dependent manner as set forth in Example 7.

As shown in FIG. 20, PEGylated TPO Compound No. 1 activated Baf/3 cells recombinantly expressing human TPO-R in a dose dependent fashion. As shown in FIG. 21, stronger activation of TPO-R was observed when the cells were stimulated with the PEGylated TPO Compound No. 1 than TPO at the same concentration. The $EC_{50}$ for PEGylated TPO Compound No. 1 was about 5 pM.

Although only preferred embodiments of the invention are specifically described above, it will be appreciated that modifications and variations of the invention are possible without departing from the spirit and intended scope of the invention.

What is claimed is:

1. A method of preventing the development of anemia following treatment selected from the group consisting of treatment with a cytotoxic agent, treatment with an antitumor agent and treatment with radiation comprising administering an effective amount of a TPO peptide compound to a subject in need thereof, said TPO peptide compound comprising the following structure:

I E G P T L R Q (2-Nal) L A A R (Sar).     (SEQ ID NO:5)

2. The method of claim 1, wherein said effective amount is from about 1 ug to about 300 µg/kg of body weight per day.

3. A method of increasing the production of red blood cells comprising administering an effective amount of a TPO peptide compound to a subject, said TPO peptide compound comprising the following structure:

I E G P T L R Q (2-Nal) L A A R (Sar).     (SEQ ID NO:5)

4. The method of claim 3, wherein said method comprises increasing the production of precursors to said red blood cells.

5. A method of treating anemia, comprising a step of administering an effective amount of a TPO peptide compound to a subject in need thereof, said TPO peptide compound comprising the following structure:

I E G P T L R Q (2-Nal) L A A R (Sar).     (SEQ ID NO:5)

6. The method of claim 1, wherein said TPO peptide compound comprises the following structure:

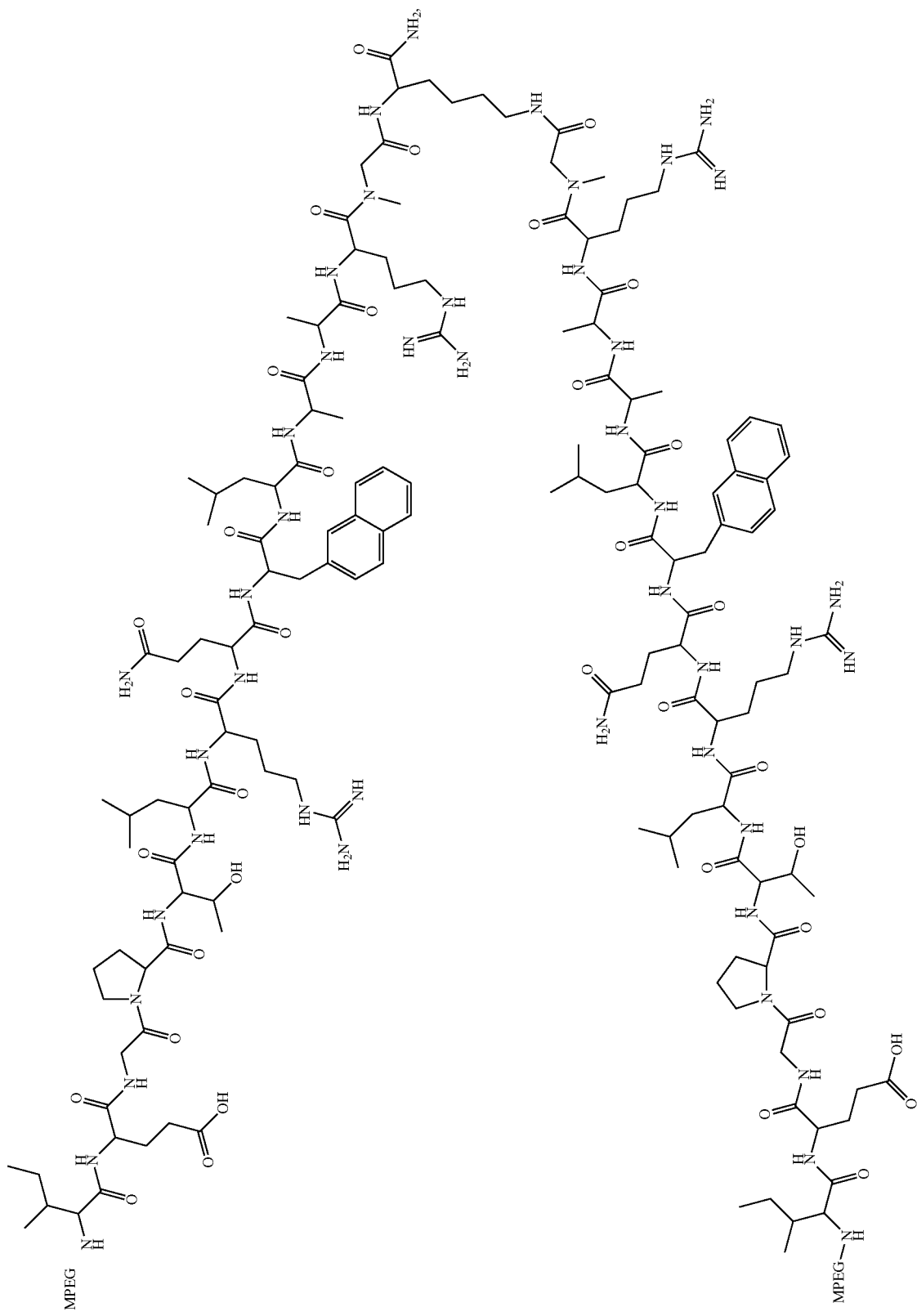

wherein MPEG is methoxypoly(ethylene glycol) having a molecular weight of approximately 20,000 Daltons.

7. The method of claim 6, wherein said effective amount is from about 1 ug to about 300 μg/kg of body weight per day.

8. The method of claim 3, wherein said TPO peptide compound comprises the following structure:

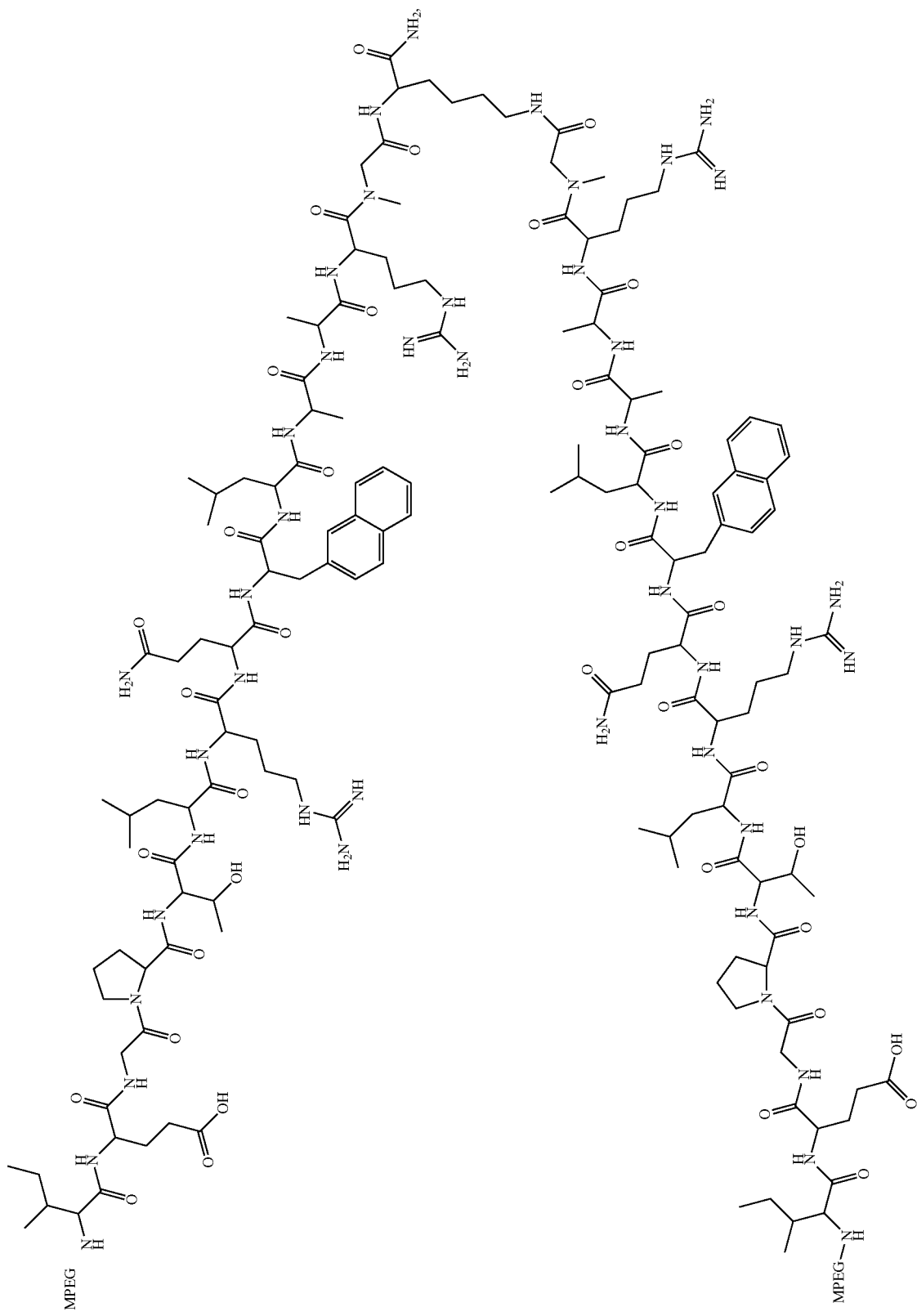

wherein MPEG is methoxypoly(ethylene glycol) having a molecular weight of approximately 20,000 Daltons.

9. The method of claim 8, wherein said method comprises increasing the production of precursors to said red blood cells.

10. The method of claim 5, wherein said TPO peptide compound comprises the following structure:

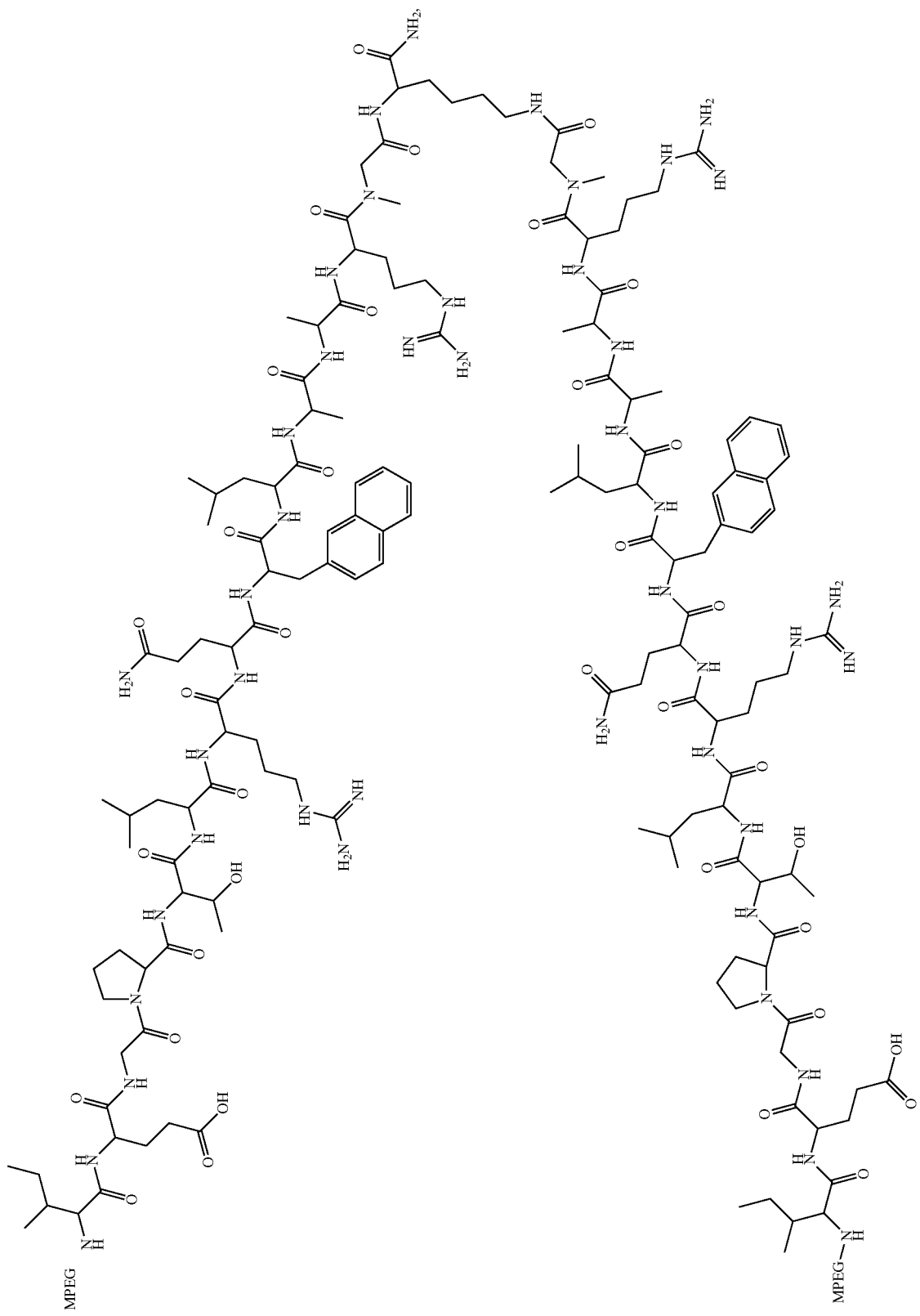

wherein MPEG is methoxypoly(ethylene glycol) having a molecular weight of approximately 20,000 Daltons.

11. The method of claim 1, wherein said TPO peptide compound comprises the following structure:

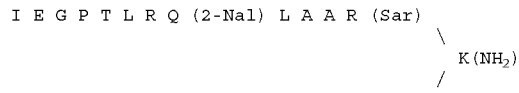

-continued

I E G P T L R Q (2-Nal) L A A R (Sar).

12. The method of claim 11, wherein said effective amount is from about 1 ug to about 300 µg/kg of body weight per day.

13. The method of claim 11, wherein said method comprises increasing the production of red blood cells or precursors to said red blood cells.

* * * * *

UNITED STATES PATENT AND TRADEMARK OFFICE
CERTIFICATE OF CORRECTION

| | | |
|---|---|---|
| PATENT NO. | : 7,615,533 B2 | Page 1 of 1 |
| APPLICATION NO. | : 11/354065 | |
| DATED | : November 10, 2009 | |
| INVENTOR(S) | : Yurkow et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this

Sixteenth Day of November, 2010

David J. Kappos
*Director of the United States Patent and Trademark Office*